(12) United States Patent
Maienfisch et al.

(10) Patent No.: US 8,420,855 B2
(45) Date of Patent: Apr. 16, 2013

(54) INSECTICIDAL COMPOUNDS

(75) Inventors: Peter Maienfisch, Stein (CH); Werner Zambach, Stein (CH); Pierre Jung, Stein (CH); William Lutz, Riehen (CH); Thomas Pitterna, Stein (CH); Peter Renold, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 717 days.

(21) Appl. No.: 12/306,545

(22) PCT Filed: Jun. 26, 2007

(86) PCT No.: PCT/EP2007/005641
§ 371 (c)(1),
(2), (4) Date: Oct. 2, 2009

(87) PCT Pub. No.: WO2008/000438
PCT Pub. Date: Jan. 3, 2008

(65) Prior Publication Data
US 2010/0048715 A1  Feb. 25, 2010

(30) Foreign Application Priority Data

Jun. 27, 2006 (GB) .................................. 0612713.8

(51) Int. Cl.
*C07C 327/18* (2006.01)
(52) U.S. Cl.
USPC ......................................................... 564/74
(58) Field of Classification Search ........ 564/74
See application file for complete search history.

(56) References Cited

U.S. PATENT DOCUMENTS 6,194,418 B1  2/2001  Seitz et al.
6,548,549 B1  4/2003  Seitz et al.

FOREIGN PATENT DOCUMENTS

| CA | 2554437 A1 | 8/2005 |
| EP | 1275653 A | 1/2003 |
| EP | 1661886 A1 | 5/2006 |
| JP | 09278731 A | 10/1997 |

*Primary Examiner* — Taofiq A Solola
(74) *Attorney, Agent, or Firm* — Dana S. Rewoldt

(57) ABSTRACT

A compound of formula (I), wherein $A^1, A^2, A^3, A^4, R^1, R^2, G^1, G^2, Q^1$ and $Q^2$ are as defined in claim 1; or salts or N-oxides thereof. Furthermore, the present invention relates to processes and intermediates for preparing compounds of formula (I), to insecticidal, acaricidal, molluscicidal and nematicidal compositions comprising them and to methods of using them to combat and control insect, acarine, mollusc and nematode pests.

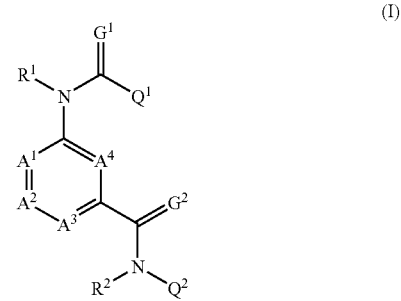

(I)

21 Claims, No Drawings

INSECTICIDAL COMPOUNDS

This application is a 371 of International Application No. PCT/EP2007/005641 filed Jun. 26, 2007, which claims priority to GB 0612713.8 filed Jun. 27, 2006, the contents of which are incorporated herein by reference.

The present invention relates to certain bisamide derivatives, to processes and intermediates for preparing them, to insecticidal, acaricidal, molluscicidal and nematicidal compositions comprising them and to methods of using them to combat and control insect, acarine, mollusc and nematode pests.

Aromatic bisamide derivatives with insecticidal properties are disclosed in, for example, WO 05/073165, JP 2006/306771, WO 06/137376, WO 06/137394 and WO 07/017,075.

It has now surprisingly been found that certain novel bisamide derivatives have improved insecticidal properties.

The present invention therefore provides a compound of formula (I):

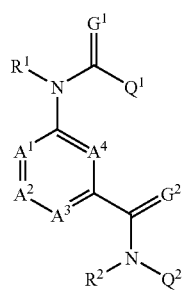

wherein
$A^1$, $A^2$, $A^3$ and $A^4$ are independently of one another C—X—$R^3$, C—$R^5$ or nitrogen, provided that at least one of $A^1$, $A^2$, $A^3$ and $A^4$ is C—X—$R^3$ and no more than two of $A^1$, $A^2$, $A^3$ and $A^4$ are nitrogen;
$R^1$ and $R^2$ are independently of one another hydrogen, $C_1$-$C_4$alkyl or $C_1$-$C_4$alkylcarbonyl;
$G^1$ and $G^2$ are independently of one another oxygen or sulfur;
each $R^3$ is independently hydrogen, $C_1$-$C_{12}$alkyl, $C_1$-$C_{12}$haloalkyl, $C_2$-$C_8$alkenyl, $C_2$-$C_8$alkynyl, aryl or aryl substituted by halogen or $C_1$-$C_4$alkyl, or heterocyclyl or heterocyclyl substituted by halogen or $C_1$-$C_4$alkyl;
each X is independently oxygen, sulfur or N—$R^4$; wherein each $R^4$ is independently hydrogen, $C_1$-$C_4$alkyl or $C_1$-$C_4$alkylcarbonyl;
each $R^5$ is independently hydrogen, halogen, $C_1$-$C_4$alkyl or trifluoromethyl;
$Q^1$ is aryl or aryl substituted by one to five substituents $R^6$, which may be the same or different, or $Q^1$ is heterocyclyl or heterocyclyl substituted by one to five substituents $R^6$, which may be the same or different; wherein
each $R^6$ is independently cyano, nitro, hydroxy, halogen, $C_1$-$C_4$alkyl, $C_1$-$C_4$haloalkyl, $C_2$-$C_4$alkenyl, $C_2$-$C_4$ haloalkenyl, $C_2$-$C_4$alkynyl, $C_2$-$C_4$haloalkynyl, $C_3$-$C_6$cycloalkyl, $C_3$-$C_6$halocycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$ haloalkylsulfonyl, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$ alkoxycarbonyl, $C_1$-$C_4$alkylcarbonylamino or phenyl; and $Q^2$ is a moiety of formula (II) or (III)

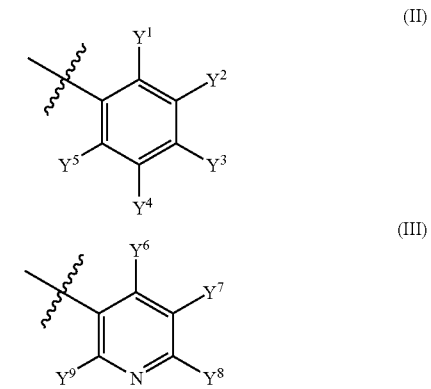

wherein
$Y^1$ and $Y^5$ are independently of each other cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$ haloalkylsulfonyl;
$Y^3$ is $C_2$-$C_6$perfluoroalkyl, $C_1$-$C_6$perfluoroalkylthio, $C_1$-$C_6$ perfluoroalkylsulfinyl or $C_1$-$C_6$perfluoroalkylsulfonyl;
$Y^2$ and $Y^4$ are independently of each other hydrogen, halogen or $C_1$-$C_4$alkyl;
$Y^6$ and $Y^9$ are independently of each other cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$ haloalkylsulfonyl;
$Y^8$ is $C_1$-$C_4$haloalkoxy, $C_2$-$C_6$perfluoroalkyl, $C_1$-$C_6$ perfluoroalkylthio, $C_1$-$C_6$perfluoroalkyl-sulfinyl or $C_1$-$C_6$ perfluoroalkylsulfonyl;
$Y^7$ is hydrogen, halogen or $C_1$-$C_4$alkyl;
or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxy-carbonyl, alkylcarbonyl) is a straight or branched chain and is, for example, methyl, ethyl, n-propyl, n-butyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$. Perfluoroalkyl groups (either alone or as part of a larger group, such as perfluoroalkylthio) are a particular type of haloalkyl group; they are alkyl groups which are completely substituted with fluorine atoms and are, for example, —$CF_3$, —$CF_2CF_3$ or —$CF(CF_3)_2$.

Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CCl=CClF or —CHClC≡CH.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl, 2,2-dichloro-1-methyl-cyclopropyl and 2-chloro-4-fluorocyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine. Examples of bicyclic groups are benzothiophenyl, benzimidazolyl, benzothiadiazolyl, quinolinyl, cinnolinyl and quinoxalinyl.

The term "heterocyclyl" is defined to include heteroaryl and in addition their unsaturated or partially unsaturated analogues such as piperidinyl, 1,3-dioxolanyl, 1,3-dioxanyl, 4,5-dihydro-isoxazolyl, tetrahydrofuranyl and morpholinyl.

Preferred values of $A^1$, $A^2$, $A^3$, $A^4$, $R^1$, $R^2$, $G^1$, $G^2$, $R^3$, X, $R^4$, $R^5$, $Q^1$, $R^6$, $Q^2$, $Y^1$, $Y^2$, $Y^3$, $Y^4$, $Y^5$, $Y^6$, $Y^7$, $Y^8$ and $Y^9$ are, in any combination, as set out below.

Preferably $A^1$ is C—X—$R^3$ or C—$R^5$.
Preferably $A^2$ is C—X—$R^3$ or C—$R^5$.
Preferably $A^3$ is C—X—$R^3$ or C—$R^5$.
Preferably $A^4$ is C—X—$R^3$ or C—$R^5$.
Preferably one, two or three of $A^1$, $A^2$, $A^3$ and $A^4$ are C—X—$R^3$.
More preferably one or two of $A^1$, $A^2$, $A^3$ and $A^4$ are C—X—$R^3$.
Most preferably one of $A^1$, $A^2$, $A^3$ and $A^4$ is C—X—$R^3$.
Preferably $R^1$ is hydrogen, methyl, ethyl or acetyl.
More preferably $R^1$ is hydrogen, methyl or ethyl.
Even more preferably $R^1$ is hydrogen or ethyl.
Most preferably $R^1$ is hydrogen.
Preferably $R^2$ is hydrogen, methyl, ethyl or acetyl.
More preferably $R^2$ is hydrogen, methyl or ethyl.
Even more preferably $R^2$ is hydrogen or ethyl.
Most preferably $R^2$ is hydrogen.
Preferably $G^1$ is oxygen.
Preferably $G^2$ is oxygen.
Preferably each $R^3$ is independently hydrogen, $C_1$-$C_4$alkyl, $C_1$-$C_4$haloalkyl, $C_2$-$C_4$alkenyl, $C_2$-$C_4$alkynyl, phenyl or phenyl substituted by one to three substituents independently selected from halogen or $C_1$-$C_4$alkyl.

More preferably each $R^3$ is independently hydrogen, methyl, ethyl, n-propyl, allyl, phenyl or phenyl mono-substituted by halogen or methyl.
Even more preferably each $R^3$ is independently hydrogen, methyl or ethyl.
Most preferably each $R^3$ is independently hydrogen or methyl.
Preferably each X is independently oxygen or sulfur.
Most preferably each X is oxygen.
Preferably each $R^4$ is independently hydrogen or methyl.
Preferably each $R^5$ is independently hydrogen, fluoro, methyl or trifluoromethyl.
More preferably each $R^5$ is independently hydrogen or fluoro.
Most preferably each $R^5$ is hydrogen.
Preferably $Q^1$ is phenyl, pyridyl, furanyl, thiophenyl, pyrazolyl or 1,2,3-thiadiazolyl, or phenyl, pyridyl, furanyl, thiophenyl, pyrazolyl or 1,2,3-thiadiazolyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such groups for $Q^1$ are 5-bromo-furan-2-yl, 2-bromo-phenyl, 5-bromo-pyrid-3-yl, 2-chloro-5-nitro-phenyl, 2-chloro-phenyl, 3-chloro-phenyl, 2-chloro-pyrid-3-yl, 2-chloro-pyrid-4-yl, 6-chloro-pyrid-3-yl, 5-chloro-thiophen-2-yl, 3-chloro-5-trifluoromethyl-pyrid-2-yl, 4-cyano-phenyl, 2,5-dichloro-phenyl, 2,3-difluoro-phenyl, 1,3-dimethyl-pyrazol-5-yl, 4-fluoro-phenyl, 2-fluoro-pyrid-3-yl, 2-fluoro-3-trifluoromethyl-phenyl, 2-methyl-phenyl, 3-methyl-pyrid-2-yl, 2-methylthio-pyrid-3-yl, 4-nitro-phenyl, phenyl, 1,2,3-thiadiazol-4-yl and thiophen-2-yl.

More preferably $Q^1$ is phenyl or pyridyl, or phenyl or pyridyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such preferred groups for $Q^1$ are 2-chloro-phenyl, 3-chloro-phenyl, 2-chloro-pyrid-3-yl, 2-chloro-pyrid-4-yl, 6-chloro-pyrid-3-yl, 3-chloro-5-trifluoromethyl-pyrid-2-yl, 4-cyano-phenyl, 2,5-dichloro-phenyl, 2,3-difluoro-phenyl, 4-fluoro-phenyl, 2-fluoro-pyrid-3-yl, 2-fluoro-3-trifluoromethyl-phenyl, 2-methyl-phenyl, 3-methyl-pyrid-2-yl, 2-methylthio-pyrid-3-yl and phenyl.

Even more preferably $Q^1$ is phenyl substituted by one substituent selected from cyano, fluoro or chloro. Examples of even more preferred groups for $Q^1$ are 2-chloro-phenyl, 3-chloro-phenyl, 4-cyano-phenyl and 4-fluoro-phenyl.

Most preferably $Q^1$ is 4-fluoro-phenyl.

Each $R^6$ is independently cyano, nitro, hydroxy, halogen, $C_1$-$C_4$alkyl, $C_1$-$C_4$haloalkyl, $C_1$-$C_3$alkoxy, $C_1$-$C_3$haloalkoxy, $C_1$-$C_3$alkylthio, $C_1$-$C_3$haloalkylthio, $C_1$-$C_4$alkylamino or di-($C_1$-$C_4$alkyl)-amino.

A particularly preferred group of compounds are compounds of formula (I) wherein $Q^1$ is aryl or aryl substituted by one to five substituents $R^6$, which may be the same or different.

Preferably $Q^1$ is phenyl or phenyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such groups for $Q^1$ are 2-bromo-phenyl, 2-chloro-5-nitro-phenyl, 2-chloro-phenyl, 3-chloro-phenyl, 4-cyano-phenyl, 2,5-dichloro-phenyl, 2,3-difluoro-phenyl, 4-fluoro-phenyl, 2-fluoro-3-trifluoromethyl-phenyl, 2-methyl-phenyl, 4-nitro-phenyl and phenyl.

More preferably $Q^1$ is phenyl or phenyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such preferred groups for $Q^1$ are 2-chloro-phenyl, 3-chloro-phenyl, 4-cyano-phenyl, 2,5-dichloro-phenyl, 2,3-difluoro-phenyl, 4-fluoro-phenyl, 2-fluoro-3-trifluoromethyl-phenyl, 2-methyl-phenyl and phenyl.

Another particularly preferred group of compounds are compounds of formula (I) wherein $Q^1$ is heterocyclyl or heterocyclyl substituted by one to five substituents $R^6$, which may be the same or different. The heterocyclyl group is preferably a heteroaryl group.

Preferably $Q^1$ is pyridyl, furanyl, thiophenyl, pyrazolyl or 1,2,3-thiadiazolyl, or pyridyl, furanyl, thiophenyl, pyrazolyl or 1,2,3-thiadiazolyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such groups for $Q^1$ are 5-bromo-furan-2-yl, 5-bromo-pyrid-3-yl, 2-chloro-pyrid-3-yl, 2-chloro-pyrid-4-yl, 6-chloro-pyrid-3-yl, 5-chloro-thiophen-2-yl, 3-chloro-5-trifluoromethyl-pyrid-2-yl, 1,3-dimethyl-pyrazol-5-yl, 2-fluoro-pyrid-3-yl, 3-methyl-pyrid-2-yl, 2-methylthio-pyrid-3-yl, 1,2,3-thiadiazol-4-yl and thiophen-2-yl.

More preferably $Q^1$ is pyridyl or pyridyl substituted by one to three substituents independently selected from cyano, nitro, hydroxy, fluoro, chloro, bromo, methyl, trifluoromethyl, methoxy, methylthio, methylsulfinyl, methylsulfonyl or phenyl. Examples of such preferred groups for $Q^1$ are 2-chloro-pyrid-3-yl, 2-chloro-pyrid-4-yl, 6-chloro-pyrid-3-yl, 3-chloro-5-trifluoromethyl-pyrid-2-yl, 2-fluoro-pyrid-3-yl, 3-methyl-pyrid-2-yl and 2-methylthio-pyrid-3-yl.

Preferably $Q^2$ is a moiety of formula (II). Especially preferred groups for $Q^2$ are 4-heptafluoroisopropyl-2,6-dimethyl-phenyl, 4-heptafluoroisopropyl-2,6-diethyl-phenyl and 4-heptafluoroisopropyl-2-methoxymethyl-6-methyl-phenyl.

Preferably $Y^1$ is cyano, chloro, methyl, ethyl, trifluoromethyl or methoxymethyl.

More preferably $Y^1$ is cyano, chloro, methyl or trifluoromethyl.

Even more preferably $Y^1$ is methyl or ethyl.
Most preferably $Y^1$ is methyl.
Preferably $Y^2$ is hydrogen, fluoro, chloro or methyl.
Most preferably $Y^2$ is hydrogen.
Preferably $Y^3$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.
Most preferably $Y^3$ is heptafluoroprop-2-yl.
Preferably $Y^4$ is hydrogen, fluoro, chloro or methyl.
Most preferably $Y^4$ is hydrogen.
Preferably $Y^5$ is cyano, chloro, methyl, ethyl or trifluoromethyl.
More preferably $Y^5$ is cyano, chloro, methyl or trifluoromethyl.
Even more preferably $Y^5$ is methyl or ethyl.
Most preferably $Y^5$ is methyl.
Preferably $Y^6$ is cyano, chloro, methyl, ethyl or trifluoromethyl.
More preferably $Y^6$ is methyl or ethyl.
Most preferably $Y^6$ is methyl.
Preferably $Y^7$ is hydrogen, fluoro, chloro or methyl.
Most preferably $Y^7$ is hydrogen.
Preferably $Y^8$ is heptafluoropropyl, heptafluoroprop-2-yl, heptafluoropropylthio, heptafluoropropylsulfinyl, heptafluoropropylsulfonyl, heptafluoroprop-2-ylthio, heptafluoroprop-2-ylsulfinyl, heptafluoroprop-2-ylsulfonyl or nonafluorobut-2-yl.

Most preferably $Y^8$ is heptafluoroprop-2-yl.
Preferably $Y^9$ is cyano, chloro, methyl, ethyl or trifluoromethyl.
More preferably $Y^9$ is methyl or ethyl.
Most preferably $Y^9$ is methyl.

In one embodiment of the invention $Y^1$ and $Y^5$ are independently of each other cyano, halogen, $C_1$-$C_4$alkyl, $C_1$-$C_4$haloalkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl.

In one embodiment of the invention $Y^6$ and $Y^9$ are independently of each other cyano, halogen, $C_1$-$C_4$alkyl, $C_1$-$C_4$haloalkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl.

In one embodiment the invention provides a novel compound of formula (Ia)

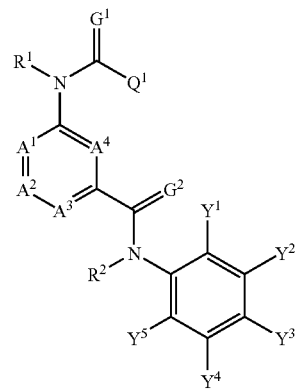

(Ia)

wherein $A^1$, $A^2$, $A^3$, $A^4$, $R^1$, $R^2$, $G^1$, $G^2$, $Q^1$, $Y^1$, $Y^2$, $Y^3$, $Y^4$ and $Y^5$ are as defined in relation to formula I; or salts or N-oxides thereof. The preferences for $A^1$, $A^2$, $A^3$, $A^4$, $R^1$, $R^2$, $G^1$, $G^2$, $Q^1$, $Y^1$, $Y^2$, $Y^3$, $Y^4$ and $Y^5$ are the same as the preferences set out for the corresponding substituents of the compounds of the formula (I).

In another embodiment the invention provides a novel compound of formula (Ib)

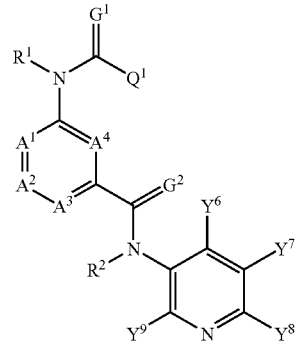

(Ib)

wherein $A^1, A^2, A^3, A^4, R^1, R^2, G^1, G^2, Q^1, Y^6, Y^7, Y^8$ and $Y^9$ are as defined in relation to formula I; or salts or N-oxides thereof. The preferences for $A^1, A^2, A^3, A^4, R^1, R^2, G^1, G^2, Q^1, Y^6, Y^7, Y^8$ and $Y^9$ are the same as the preferences set out for the corresponding substituents of the compounds of the formula (I).

In yet another embodiment the invention provides a novel compound of formula (Ic):

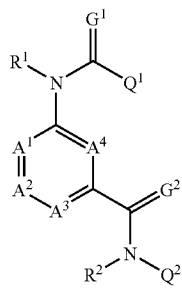

(Ic)

wherein $A^1, A^2, A^3, A^4, R^1, R^2, G^1, G^2, Q^1$ and $Q^2$ are as defined in relation to formula I, and each X is independently oxygen or sulfur; or salts or N-oxides thereof. The preferences for $A^1, A^2, A^3, A^4, R^1, R^2, G^1, G^2, Q^1$ and $Q^2$ are the same as the preferences set out for the corresponding substituents of the compounds of the formula (I).

In a further embodiment the invention provides a novel compound of formula (Ic) wherein $A^1, A^2, A^3, A^4, R^1, R^2, G^1, G^2, Q^1$ and $Q^2$ are as defined in relation to formula I, and each X is oxygen; or salts or N-oxides thereof. The preferences for $A^1, A^2, A^3, A^4, R^1, R^2, G^1, G^2, Q^1$ and $Q^2$ are the same as the preferences set out for the corresponding substituents of the compounds of the formula (I). A group of particularly preferred compounds are compounds of formula (Ic) wherein $X^1$, $X^3$ and $X^4$ are hydrogen and $X^2$ is hydroxy. A further group of particularly preferred compounds are compounds of formula (Ic) wherein $X^1$, $X^2$ and $X^3$ are hydrogen and $X^4$ is hydroxy. Another group of particularly preferred compounds are compounds of formula (Ic) wherein $X^1$, $X^2$ and $X^3$ are hydrogen and $X^4$ is allyloxy. A further group of particularly preferred compounds are compounds of formula (Ic) wherein $X^1$ and $X^3$ are both hydrogen and $X^2$ and $X^4$ are both hydroxy.

In yet a further embodiment the present invention provides a novel compound of formula (Ic) wherein $A^1, A^2, A^3, A^4, R^1, R^2, G^1, G^2, Q^1$ and $Q^2$ are as defined in relation to formula I, and each X is sulfur; or salts or N-oxides thereof. The preferences for $A^1, A^2, A^3, A^4, R^1, R^2, G^1, G^2, Q^1$ and $Q^2$ are the same as the preferences set out for the corresponding substituents of the compounds of the formula (I). A group of particularly preferred compounds are compounds of formula (Ic) wherein $X^2$, $X^3$ and $X^4$ are hydrogen and $X^1$ is methylthio.

In another embodiment the invention provides a novel compound of formula (Ic) wherein $A^1, A^2, A^3, A^4, R^1, R^2, G^1, G^2, Q^1$ and $Q^2$ are as defined in relation to formula I, and each X is N—R^4 wherein $R^4$ is as defined in relation to formula I; or salts or N-oxides thereof. The preferences for $A^1, A^2, A^3, A^4, R^1, R^2, G^1, G^2, Q^1$ and $Q^2$ are the same as the preferences set out for the corresponding substituents of the compounds of the formula (I). A group of particularly preferred compounds are compounds of formula (Ic) wherein $X^2$, $X^3$ and $X^4$ are hydrogen and $X^1$ is N,N-dimethylamino. A further group of particularly preferred compounds are compounds of formula (Ic) wherein $X^1$, $X^2$ and $X^4$ are hydrogen and $X^3$ is N,N-dimethylamino. Another group of particularly preferred compounds are compounds of formula (Ic) wherein $X^2$, $X^3$ and $X^4$ are hydrogen and $X^1$ is N-ethylamino. A further group of particularly preferred compounds are compounds of formula (Ic) wherein $X^1$, $X^2$ and $X^4$ are hydrogen and $X^3$ is N-ethylamino.

Certain intermediates are novel and as such form a further aspect of the invention.

One group of novel intermediates are aromatic compounds of formula (Id)

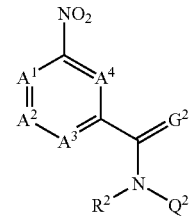

(Id)

wherein $A^1, A^2, A^3, A^4, R^2, G^2$ and $Q^2$ are as defined in relation to formula I; or salts or N-oxides thereof. The preferences for $A^1, A^2, A^3, A^4, R^2, G^2$ and $Q^2$ are the same as the preferences set out for the corresponding substituents of the compounds of the formula (I).

Another group of novel intermediates are aromatic compounds of formula (Ie)

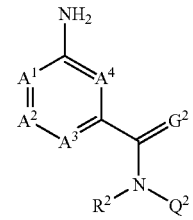

(Ie)

wherein $A^1, A^2, A^3, A^4, R^2, G^2$ and $Q^2$ are as defined in relation to formula I; or salts or N-oxides thereof. The preferences for $A^1, A^2, A^3, A^4, R^2, G^2$ and $Q^2$ are the same as the preferences set out for the corresponding substituents of the compounds of the formula (I).

The compounds in Tables 1 to 27 below illustrate the compounds of the invention.

TABLE 1

Table 1 provides 119 compounds of formula (If) wherein Q¹ is 5-bromo-furan-2-yl.

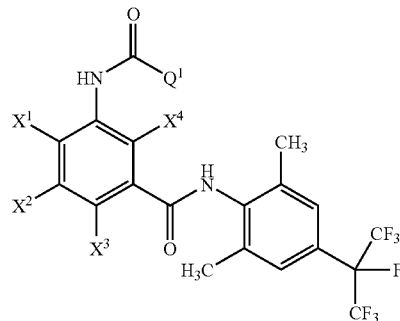

(If)

| Compound number | X¹ | X² | X³ | X⁴ |
|---|---|---|---|---|
| 1.001 | HO— | H | H | H |
| 1.002 | H | HO— | H | H |
| 1.003 | H | H | HO— | H |
| 1.004 | H | H | H | HO— |
| 1.005 | MeO— | H | H | H |
| 1.006 | H | MeO— | H | H |
| 1.007 | H | H | MeO— | H |
| 1.008 | H | H | H | MeO— |
| 1.009 | MeO— | H | H | MeO— |
| 1.010 | H | MeO— | H | MeO— |
| 1.011 | H | H | MeO— | MeO— |
| 1.012 | PhO— | H | H | H |
| 1.013 | H | PhO— | H | H |
| 1.014 | H | H | PhO— | H |
| 1.015 | H | H | H | PhO— |
| 1.016 | m-Me-PhO— | H | H | H |
| 1.017 | H | m-Me-PhO— | H | H |
| 1.018 | H | H | m-Me-PhO— | H |
| 1.019 | H | H | H | m-Me-PhO— |
| 1.020 | p-Cl—PhO— | H | H | H |
| 1.021 | H | p-Cl—PhO— | H | H |
| 1.022 | H | H | p-Cl—Pho— | H |
| 1.023 | H | H | H | p-Cl—PhO— |
| 1.024 | HO— | F | H | H |
| 1.025 | HO— | H | F | H |
| 1.026 | HO— | H | H | F |
| 1.027 | F | HO— | H | H |
| 1.028 | H | HO— | F | H |
| 1.029 | H | HO— | H | F |
| 1.030 | F | H | HO— | H |
| 1.031 | H | F | HO— | H |
| 1.032 | H | H | HO— | F |
| 1.033 | F | H | H | HO— |
| 1.034 | H | F | H | HO— |
| 1.035 | H | H | F | HO— |
| 1.036 | MeO— | F | H | H |
| 1.037 | MeO— | H | F | H |
| 1.038 | MeO— | H | H | F |
| 1.039 | F | MeO— | H | H |
| 1.040 | H | MeO— | F | H |
| 1.041 | H | MeO— | H | F |
| 1.042 | F | H | MeO— | H |
| 1.043 | H | F | MeO— | H |
| 1.044 | H | H | MeO— | F |
| 1.045 | F | H | H | MeO— |
| 1.046 | H | F | H | MeO— |
| 1.047 | H | H | F | MeO— |
| 1.048 | PhO— | F | H | H |
| 1.049 | PhO— | H | F | H |
| 1.050 | PhO— | H | H | F |
| 1.051 | F | PhO— | H | H |
| 1.052 | H | PhO— | F | H |
| 1.053 | H | PhO— | H | F |
| 1.054 | F | H | PhO— | H |
| 1.055 | H | F | PhO— | H |
| 1.056 | H | H | PhO— | F |

TABLE 1-continued

Table 1 provides 119 compounds of formula (If) wherein $Q^1$ is 5-bromo-furan-2-yl.

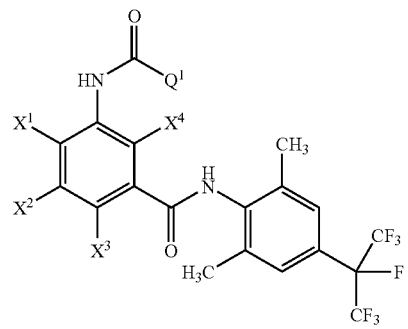

(If)

| Compound number | $X^1$ | $X^2$ | $X^3$ | $X^4$ |
|---|---|---|---|---|
| 1.057 | F | H | H | PhO— |
| 1.058 | H | F | H | PhO— |
| 1.059 | H | H | F | PhO— |
| 1.060 | MeS— | H | H | H |
| 1.061 | H | MeS— | H | H |
| 1.062 | H | H | MeS— | H |
| 1.063 | H | H | H | MeS— |
| 1.064 | PhS— | H | H | H |
| 1.065 | H | PhS— | H | H |
| 1.066 | H | H | PhS— | H |
| 1.067 | H | H | H | PhS— |
| 1.068 | p-Me-PhS— | H | H | H |
| 1.069 | H | p-Me-PhS— | H | H |
| 1.070 | H | H | p-Me-PhS— | H |
| 1.071 | H | H | H | p-Me-PhS— |
| 1.072 | m-F—PhS— | H | H | H |
| 1.073 | H | m-F—PhS— | H | H |
| 1.074 | H | H | m-F—PhS— | H |
| 1.075 | H | H | H | m-F—PhS— |
| 1.076 | MeS— | F | H | H |
| 1.077 | MeS— | H | F | H |
| 1.078 | MeS— | H | H | F |
| 1.079 | F | MeS— | H | H |
| 1.080 | H | MeS— | F | H |
| 1.081 | H | MeS— | H | F |
| 1.082 | F | H | MeS— | H |
| 1.083 | H | F | MeS— | H |
| 1.084 | H | H | MeS— | F |
| 1.085 | F | H | H | MeS— |
| 1.086 | H | F | H | MeS— |
| 1.087 | H | H | F | MeS— |
| 1.088 | PhS— | F | H | H |
| 1.089 | PhS— | H | F | H |
| 1.090 | PhS— | H | H | F |
| 1.091 | F | PhS— | H | H |
| 1.092 | H | PhS— | F | H |
| 1.093 | H | PhS— | H | F |
| 1.094 | F | H | PhS— | H |
| 1.095 | H | F | PhS— | H |
| 1.096 | H | H | PhS— | F |
| 1.097 | F | H | H | PhS— |
| 1.098 | H | F | H | PhS— |
| 1.099 | H | H | F | PhS— |
| 1.100 | EtHN— | H | H | H |
| 1.101 | H | EtHN— | H | H |
| 1.102 | H | H | EtHN— | H |
| 1.103 | H | H | H | EtHN— |
| 1.104 | Me$_2$N— | H | H | H |
| 1.105 | H | Me2N— | H | H |
| 1.106 | H | H | Me$_2$N— | H |
| 1.107 | H | H | H | Me$_2$N— |
| 1.108 | PhHN— | H | H | H |
| 1.109 | H | PhHN— | H | H |
| 1.110 | H | H | PhHN— | H |
| 1.111 | H | H | H | PhHN— |
| 1.112 | m-Me-PhHN— | H | H | H |

TABLE 1-continued

Table 1 provides 119 compounds of formula (If) wherein $Q^1$ is 5-bromo-furan-2-yl.

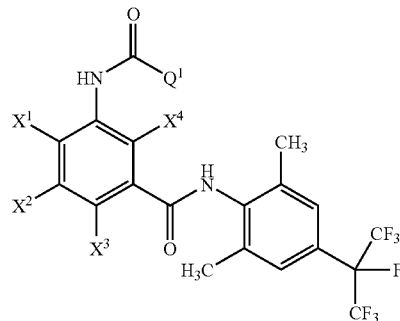

(If)

| Compound number | $X^1$ | $X^2$ | $X^3$ | $X^4$ |
|---|---|---|---|---|
| 1.113 | H | m-Me-PhHN— | H | H |
| 1.114 | H | H | m-Me-PhHN— | H |
| 1.115 | H | H | H | m-Me-PhHN— |
| 1.116 | p-F—PhHN— | H | H | H |
| 1.117 | H | p-F—PhHN— | H | H |
| 1.118 | H | H | p-F—PhHN— | H |
| 1.119 | H | H | H | p-F—PhHN— |

Table 2:

Table 2 provides 119 compounds of formula (If) wherein $Q^1$ is 2-bromo-phenyl and $X^1$, $X^2$, $X^3$ and $X^4$ have the values listed in Table 1.

Table 3:

Table 3 provides 119 compounds of formula (If) wherein $Q^1$ is 5-bromo-pyrid-3-yl and $X^1$, $X^2$, $X^3$ and $X^4$ have the values listed in Table 1.

Table 4:

Table 4 provides 119 compounds of formula (If) wherein $Q^1$ is 2-chloro-phenyl and $X^1$, $X^2$, $X^3$ and $X^4$ have the values listed in Table 1.

Table 5:

Table 5 provides 119 compounds of formula (If) wherein $Q^1$ is 3-chloro-phenyl and $X^1$, $X^2$, $X^3$ and $X^4$ have the values listed in Table 1.

Table 6:

Table 6 provides 119 compounds of formula (If) wherein $Q^1$ is 2-chloro-pyrid-3-yl and $X^1$, $X^2$, $X^3$ and $X^4$ have the values listed in Table 1.

Table 7:

Table 7 provides 119 compounds of formula (If) wherein $Q^1$ is 2-chloro-pyrid-4-yl and $X^1$, $X^2$, $X^3$ and $X^4$ have the values listed in Table 1.

Table 8:

Table 8 provides 119 compounds of formula (If) wherein $Q^1$ is 6-chloro-pyrid-3-yl and $X^1$, $X^2$, $X^3$ and $X^4$ have the values listed in Table 1.

Table 9:

Table 9 provides 119 compounds of formula (If) wherein $Q^1$ is 5-chloro-thiophen-2-yl and $X^1$, $X^2$, $X^3$ and $X^4$ have the values listed in Table 1.

Table 10:

Table 10 provides 119 compounds of formula (If) wherein $Q^1$ is 3-chloro-5-trifluoromethyl-pyrid-2-yl and $X^1$, $X^2$, $X^3$ and $X^4$ have the values listed in Table 1.

Table 11:

Table 11 provides 119 compounds of formula (If) wherein $Q^1$ is 4-cyano-phenyl and $X^1$, $X^2$, $X^3$ and $X^4$ have the values listed in Table 1.

Table 12:

Table 12 provides 119 compounds of formula (If) wherein $Q^1$ is 2,5-dichloro-phenyl and $X^1$, $X^2$, $X^3$ and $X^4$ have the values listed in Table 1.

Table 13:

Table 13 provides 119 compounds of formula (If) wherein $Q^1$ is 2,3-difluoro-phenyl and $X^1$, $X^2$, $X^3$ and $X^4$ have the values listed in Table 1.

Table 14:

Table 14 provides 119 compounds of formula (If) wherein $Q^1$ is 1,3-dimethyl-pyrazol-5-yl and $X^1$, $X^2$, $X^3$ and $X^4$ have the values listed in Table 1.

Table 15:

Table 15 provides 119 compounds of formula (If) wherein $Q^1$ is 4-fluoro-phenyl and $X^1$, $X^2$, $X^3$ and $X^4$ have the values listed in Table 1.

Table 16:

Table 16 provides 119 compounds of formula (If) wherein $Q^1$ is 2-fluoro-pyrid-3-yl and $X^1$, $X^2$, $X^3$ and $X^4$ have the values listed in Table 1.

Table 17:

Table 17 provides 119 compounds of formula (If) wherein $Q^1$ is 2-fluoro-3-trifluoromethyl-phenyl and $X^1$, $X^2$, $X^3$ and $X^4$ have the values listed in Table 1.

Table 18:

Table 18 provides 119 compounds of formula (If) wherein $Q^1$ is 2-methyl-phenyl and $X^1$, $X^2$, $X^3$ and $X^4$ have the values listed in Table 1.

Table 19:

Table 19 provides 119 compounds of formula (If) wherein $Q^1$ is 3-methyl-pyrid-2-yl and $X^1$, $X^2$, $X^3$ and $X^4$ have the values listed in Table 1.

Table 20:
Table 20 provides 119 compounds of formula (If) wherein $Q^1$ is 2-methylthio-pyrid-3-yl and $X^1$, $X^2$, $X^3$ and $X^4$ have the values listed in Table 1.
Table 21:
Table 21 provides 119 compounds of formula (If) wherein $Q^1$ is 4-nitro-phenyl and $X^1$, $X^2$, $X^3$ and $X^4$ have the values listed in Table 1.
Table 22:
Table 22 provides 119 compounds of formula (If) wherein $Q^1$ is phenyl and $X^1$, $X^2$, $X^3$ and $X^4$ have the values listed in Table 1.

Table 23:
Table 23 provides 119 compounds of formula (If) wherein $Q^1$ is 1,2,3-thiadiazol-4-yl and $X^1$, $X^2$, $X^3$ and $X^4$ have the values listed in Table 1.
Table 24:
Table 24 provides 119 compounds of formula (If) wherein $Q^1$ is thiophen-2-yl and $X^1$, $X^2$, $X^3$ and $X^4$ have the values listed in Table 1.
Table 25:
Table 25 provides 119 compounds of formula (If) wherein $Q^1$ is 2-chloro-5-nitro-phenyl and $X^1$, $X^2$, $X^3$ and $X^4$ have the values listed in Table 1.

TABLE 26

Table 26 provides 119 compounds of formula (Ig).

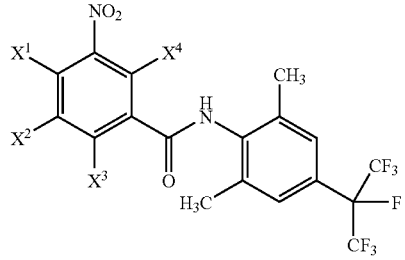

(Ig)

| Compound number | $X^1$ | $X^2$ | $X^3$ | $X^4$ |
| --- | --- | --- | --- | --- |
| 26.001 | HO— | H | H | H |
| 26.002 | H | HO— | H | H |
| 26.003 | H | H | HO— | H |
| 26.004 | H | H | H | HO— |
| 26.005 | MeO— | H | H | H |
| 26.006 | H | MeO— | H | H |
| 26.007 | H | H | MeO— | H |
| 26.008 | H | H | H | MeO— |
| 26.009 | MeO— | H | H | MeO— |
| 26.010 | H | MeO— | H | MeO— |
| 26.011 | H | H | MeO— | MeO— |
| 26.012 | PhO— | H | H | H |
| 26.013 | H | PhO— | H | H |
| 26.014 | H | H | PhO— | H |
| 26.015 | H | H | H | PhO— |
| 26.016 | m-Me-PhO— | H | H | H |
| 26.017 | H | m-Me-PhO— | H | H |
| 26.018 | H | H | m-Me-PhO— | H |
| 26.019 | H | H | H | m-Me-PhO— |
| 26.020 | p-Cl—PhO— | H | H | H |
| 26.021 | H | p-Cl—PhO— | H | H |
| 26.022 | H | H | p-Cl—Pho— | H |
| 26.023 | H | H | H | p-Cl—PhO— |
| 26.024 | HO— | F | H | H |
| 26.025 | HO— | H | F | H |
| 26.026 | HO— | H | H | F |
| 26.027 | F | HO— | H | H |
| 26.028 | H | HO— | F | H |
| 26.029 | H | HO— | H | F |
| 26.030 | F | H | HO— | H |
| 26.031 | H | F | HO— | H |
| 26.032 | H | H | HO— | F |
| 26.033 | F | H | H | HO— |
| 26.034 | H | F | H | HO— |
| 26.035 | H | H | F | HO— |
| 26.036 | MeO— | F | H | H |
| 26.037 | MeO— | H | F | H |
| 26.038 | MeO— | H | H | F |
| 26.039 | F | MeO— | H | H |
| 26.040 | H | MeO— | F | H |
| 26.041 | H | MeO— | H | F |
| 26.042 | F | H | MeO— | H |
| 26.043 | H | F | MeO— | H |
| 26.044 | H | H | MeO— | F |
| 26.045 | F | H | H | MeO— |

TABLE 26-continued

Table 26 provides 119 compounds of formula (Ig).

(Ig)

| Compound number | $X^1$ | $X^2$ | $X^3$ | $X^4$ |
|---|---|---|---|---|
| 26.046 | H | F | H | MeO— |
| 26.047 | H | H | F | MeO— |
| 26.048 | PhO— | F | H | H |
| 26.049 | PhO— | H | F | H |
| 26.050 | PhO— | H | H | F |
| 26.051 | F | PhO— | H | H |
| 26.052 | H | PhO— | F | H |
| 26.053 | H | PhO— | H | F |
| 26.054 | F | H | PhO— | H |
| 26.055 | H | F | PhO— | H |
| 26.056 | H | H | PhO— | F |
| 26.057 | F | H | H | PhO— |
| 26.058 | H | F | H | PhO— |
| 26.059 | H | H | F | PhO— |
| 26.060 | MeS— | H | H | H |
| 26.061 | H | MeS— | H | H |
| 26.062 | H | H | MeS— | H |
| 26.063 | H | H | H | MeS— |
| 26.064 | PhS— | H | H | H |
| 26.065 | H | PhS— | H | H |
| 26.066 | H | H | PhS— | H |
| 26.067 | H | H | H | PhS— |
| 26.068 | p-Me-PhS— | H | H | H |
| 26.069 | H | p-Me-PhS— | H | H |
| 26.070 | H | H | p-Me-PhS— | H |
| 26.071 | H | H | H | p-Me-PhS— |
| 26.072 | m-F—PhS— | H | H | H |
| 26.073 | H | m-F—PhS— | H | H |
| 26.074 | H | H | m-F—PhS— | H |
| 26.075 | H | H | H | m-F—PhS— |
| 26.076 | MeS— | F | H | H |
| 26.077 | MeS— | H | F | H |
| 26.078 | MeS— | H | H | F |
| 26.079 | F | MeS— | H | H |
| 26.080 | H | MeS— | F | H |
| 26.081 | H | MeS— | H | F |
| 26.082 | F | H | MeS— | H |
| 26.083 | H | F | MeS— | H |
| 26.084 | H | H | MeS— | F |
| 26.085 | F | H | H | MeS— |
| 26.086 | H | F | H | MeS— |
| 26.087 | H | H | F | MeS— |
| 26.088 | PhS— | F | H | H |
| 26.089 | PhS— | H | F | H |
| 26.090 | PhS— | H | H | F |
| 26.091 | F | PhS— | H | H |
| 26.092 | H | PhS— | F | H |
| 26.093 | H | PhS— | H | F |
| 26.094 | F | H | PhS— | H |
| 26.095 | H | F | PhS— | H |
| 26.096 | H | H | PhS— | F |
| 26.097 | F | H | H | PhS— |
| 26.098 | H | F | H | PhS— |
| 26.099 | H | H | F | PhS— |
| 26.100 | EtHN— | H | H | H |
| 26.101 | H | EtHN— | H | H |
| 26.102 | H | H | EtHN— | H |
| 26.103 | H | H | H | EtHN— |
| 26.104 | Me$_2$N— | H | H | H |
| 26.105 | H | Me2N— | H | H |

TABLE 26-continued

Table 26 provides 119 compounds of formula (Ig).

(Ig)

| Compound number | X¹ | X² | X³ | X⁴ |
|---|---|---|---|---|
| 26.106 | H | H | Me₂N— | H |
| 26.107 | H | H | H | Me₂N— |
| 26.108 | PhHN— | H | H | H |
| 26.109 | H | PhHN— | H | H |
| 26.110 | H | H | PhHN— | H |
| 26.111 | H | H | H | PhHN— |
| 26.112 | m-Me-PhHN— | H | H | H |
| 26.113 | H | m-Me-PhHN— | H | H |
| 26.114 | H | H | m-Me-PhHN— | H |
| 26.115 | H | H | H | m-Me-PhHN— |
| 26.116 | p-F—PhHN— | H | H | H |
| 26.117 | H | p-F—PhHN— | H | H |
| 26.118 | H | H | p-F—PhHN— | H |
| 26.119 | H | H | H | p-F—PhHN— |

TABLE 27

Table 27 provides 119 compounds of formula (Ih).

(Ih)

| Compound number | X¹ | X² | X³ | X⁴ |
|---|---|---|---|---|
| 27.001 | HO— | H | H | H |
| 27.002 | H | HO— | H | H |
| 27.003 | H | H | HO— | H |
| 27.004 | H | H | H | HO— |
| 27.005 | MeO— | H | H | H |
| 27.006 | H | MeO— | H | H |
| 27.007 | H | H | MeO— | H |
| 27.008 | H | H | H | MeO— |
| 27.009 | MeO— | H | H | MeO— |
| 27.010 | H | MeO— | H | MeO— |
| 27.011 | H | H | MeO— | MeO— |
| 27.012 | PhO— | H | H | H |
| 27.013 | H | PhO— | H | H |
| 27.014 | H | H | PhO— | H |
| 27.015 | H | H | H | PhO— |
| 27.016 | m-Me-PhO— | H | H | H |
| 27.017 | H | m-Me-PhO— | H | H |
| 27.018 | H | H | m-Me-PhO— | H |
| 27.019 | H | H | H | m-Me-PhO— |
| 27.020 | p-Cl—PhO— | H | H | H |
| 27.021 | H | p-Cl—PhO— | H | H |
| 27.022 | H | H | p-Cl—Pho— | H |

TABLE 27-continued

Table 27 provides 119 compounds of formula (Ih).

(Ih)

| Compound number | X¹ | X² | X³ | X⁴ |
|---|---|---|---|---|
| 27.023 | H | H | H | p-Cl—PhO— |
| 27.024 | HO— | F | H | H |
| 27.025 | HO— | H | F | H |
| 27.026 | HO— | H | H | F |
| 27.027 | F | HO— | H | H |
| 27.028 | H | HO— | F | H |
| 27.029 | H | HO— | H | F |
| 27.030 | F | H | HO— | H |
| 27.031 | H | F | HO— | H |
| 27.032 | H | H | HO— | F |
| 27.033 | F | H | H | HO— |
| 27.034 | H | F | H | HO— |
| 27.035 | H | H | F | HO— |
| 27.036 | MeO— | F | H | H |
| 27.037 | MeO— | H | F | H |
| 27.038 | MeO— | H | H | F |
| 27.039 | F | MeO— | H | H |
| 27.040 | H | MeO— | F | H |
| 27.041 | H | MeO— | H | F |
| 27.042 | F | H | MeO— | H |
| 27.043 | H | F | MeO— | H |
| 27.044 | H | H | MeO— | F |
| 27.045 | F | H | H | MeO— |
| 27.046 | H | F | H | MeO— |
| 27.047 | H | H | F | MeO— |
| 27.048 | PhO— | F | H | H |
| 27.049 | PhO— | H | F | H |
| 27.050 | PhO— | H | H | F |
| 27.051 | F | PhO— | H | H |
| 27.052 | H | PhO— | F | H |
| 27.053 | H | PhO— | H | F |
| 27.054 | F | H | PhO— | H |
| 27.055 | H | F | PhO— | H |
| 27.056 | H | H | PhO— | F |
| 27.057 | F | H | H | PhO— |
| 27.058 | H | F | H | PhO— |
| 27.059 | H | H | F | PhO— |
| 27.060 | MeS— | H | H | H |
| 27.061 | H | MeS— | H | H |
| 27.062 | H | H | MeS— | H |
| 27.063 | H | H | H | MeS— |
| 27.064 | PhS— | H | H | H |
| 27.065 | H | PhS— | H | H |
| 27.066 | H | H | PhS— | H |
| 27.067 | H | H | H | PhS— |
| 27.068 | p-Me-PhS— | H | H | H |
| 27.069 | H | p-Me-PhS— | H | H |
| 27.070 | H | H | p-Me-PhS— | H |
| 27.071 | H | H | H | p-Me-PhS— |
| 27.072 | m-F—PhS— | H | H | H |
| 27.073 | H | m-F—PhS— | H | H |
| 27.074 | H | H | m-F—PhS— | H |
| 27.075 | H | H | H | m-F—PhS— |
| 27.076 | MeS— | F | H | H |
| 27.077 | MeS— | H | F | H |
| 27.078 | MeS— | H | H | F |
| 27.079 | F | MeS— | H | H |
| 27.080 | H | MeS— | F | H |
| 27.081 | H | MeS— | H | F |
| 27.082 | F | H | MeS— | H |

TABLE 27-continued

Table 27 provides 119 compounds of formula (Ih).

(Ih)

[Structure of formula (Ih): benzamide with NH2, X1, X2, X3, X4 substituents on one ring, amide linkage to 2,6-dimethyl-4-(1,1,1,3,3,3-hexafluoro... CF3/F/CF3) phenyl group]

| Compound number | X¹ | X² | X³ | X⁴ |
|---|---|---|---|---|
| 27.083 | H | F | MeS— | H |
| 27.084 | H | H | MeS— | F |
| 27.085 | F | H | H | MeS— |
| 27.086 | H | F | H | MeS— |
| 27.087 | H | H | F | MeS— |
| 27.088 | PhS— | F | H | H |
| 27.089 | PhS— | H | F | H |
| 27.090 | PhS— | H | H | F |
| 27.091 | F | PhS— | H | H |
| 27.092 | H | PhS— | F | H |
| 27.093 | H | PhS— | H | F |
| 27.094 | F | H | PhS— | H |
| 27.095 | H | F | PhS— | H |
| 27.096 | H | H | PhS— | F |
| 27.097 | F | H | H | PhS— |
| 27.098 | H | F | H | PhS— |
| 27.099 | H | H | F | PhS— |
| 27.100 | EtHN— | H | H | H |
| 27.101 | H | EtHN— | H | H |
| 27.102 | H | H | EtHN— | H |
| 27.103 | H | H | H | EtHN— |
| 27.104 | Me₂N— | H | H | H |
| 27.105 | H | Me2N— | H | H |
| 27.106 | H | H | Me₂N— | H |
| 27.107 | H | H | H | Me₂N— |
| 27.108 | PhHN— | H | H | H |
| 27.109 | H | PhHN— | H | H |
| 27.110 | H | H | PhHN— | H |
| 27.111 | H | H | H | PhHN— |
| 27.112 | m-Me-PhHN— | H | H | H |
| 27.113 | H | m-Me-PhHN— | H | H |
| 27.114 | H | H | m-Me-PhHN— | H |
| 27.115 | H | H | H | m-Me-PhHN— |
| 27.116 | p-F—PhHN— | H | H | H |
| 27.117 | H | p-F—PhHN— | H | H |
| 27.118 | H | H | p-F—PhHN— | H |
| 27.119 | H | H | H | p-F—PhHN— |

The compounds of the invention may be made by a variety of methods.

1) Compounds of formula (I), wherein G¹ and G² are oxygen, may be made by treatment of compounds of formula (V), wherein G¹ is oxygen and R is OH, $C_1$-$C_6$alkoxy or Cl, F or Br with an amine of formula NHR²Q². When R is OH such reactions are usually carried out in the presence of a coupling reagent, such as DCC (N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)-pyridine or diisopropylethylamine, and optionally in the presence of a nucleophilic catalyst, such as hydroxybenzotriazole. When R is Cl, such reactions are usually carried out under basic conditions (for example in the presence of pyridine, triethylamine, 4-(dimethylamino)-pyridine or diisopropylethylamine), again optionally in the presence of a nucleophilic catalyst. Alternatively, it is possible to conduct the reaction in a biphasic system comprising an organic solvent, preferably ethyl acetate, and an aqueous solvent, preferably a solution of sodium bicarbonate. When R is $C_1$-$C_6$alkoxy it is sometimes possible to convert the ester directly to the amide by heating the ester and amine together in a thermal process.

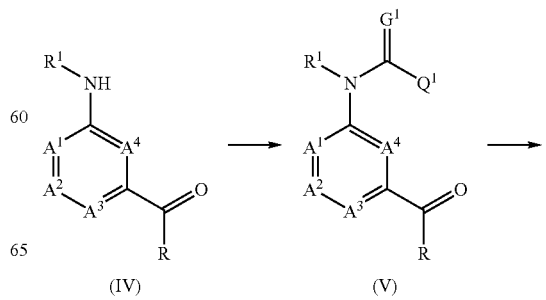

(IV)  (V)

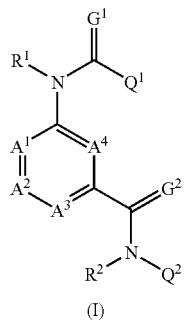

(I)

2) Acid halides of formula (V), wherein $G^1$ is oxygen and R is Cl, F or Br, may be made from carboxylic acids of formula (V), wherein $G^1$ is oxygen and R is OH, under standard conditions, such as treatment with thionyl chloride or oxalyl chloride.

3) Carboxylic acids of formula (V), wherein $G^1$ is oxygen and R is OH, may be formed from esters of formula (V), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as sodium hydroxide, in a solvent, such as ethanol.

4) Esters of formula (V), wherein $G^1$ is oxygen and R is $C_1$-$C_6$alkoxy, may be made by treatment of compounds of formula (IV), wherein R is $C_1$-$C_6$alkoxy, by acylation with a carboxylic acid of formula $Q^1$-COOH or an acid halide of formula $Q^1$-COHal, wherein Hal is Cl, F or Br, under standard conditions as described in 1).

5) Compounds of formula (IV), wherein R is $C_1$-$C_6$alkoxy, may be made from compounds of formula (VI) by sequential treatment with an alcohol R—OH under acidic conditions and then formation of the N—$R^1$ bond. It is known to a person skilled in the art that there are many reported methods for the formation of this bond depending on the nature of the substituent $R^1$.

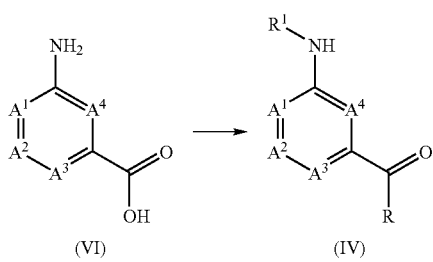

For example, reductive amination may be achieved by treatment of the amine with an aldehyde or ketone and a reducing agent such as sodium cyanoborohydride. Alternatively alkylation may be achieved by treating the amine with an alkylating agent such as an alkyl halide, optionally in the presence of a base. Alternatively arylation may be achieved by treatment of the amine with an aryl halide or sulfonate in the presence of a suitable catalyst/ligand system, often a palladium (0) complex.

6) Alternatively, compounds of formula (IV), wherein R is $C_1$-$C_6$alkoxy, may be made from a compound of formula (VII), wherein R is $C_1$-$C_6$alkoxy and LG is a leaving group, such as fluoro, chloro or sulfonate, via nucleophilic displacement of the leaving group by an amine of formula $R^1$—$NH_2$.

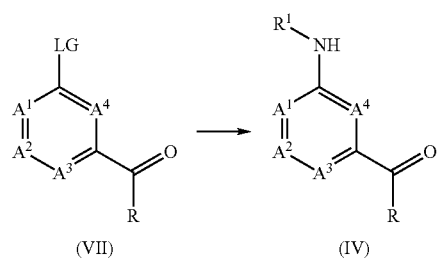

Compounds of formula (VII) and amines of formula $R^1$—$NH_2$ are either known compounds or may be made by methods known to a person skilled in the art.

7) Compounds of formula (I), wherein $G^1$ and $G^2$ are sulfur, may be made from compounds of formula (I), wherein $G^1$ and $G^2$ are oxygen, by treatment with a thio-transfer reagent, such as Lawesson's reagent or phosphorus pentasulfide.

8) Compounds of formula (I), wherein $G^1$ is sulfur and $G^2$ is oxygen, may be made from compounds of formula (V), wherein $G^1$ is oxygen and R is OH or $C_1$-$C_6$alkoxy, by treatment with a thio-transfer reagent, such as Lawessen's reagent or phosphorus pentasulfide, prior to coupling with the amine of formula $NHR^2Q^2$.

9) Alternatively, compounds of formula (I), wherein $G^1$ and $G^2$ are oxygen, may be made by the treatment of compounds of formula (IX), wherein $G^2$ is oxygen, with a carboxylic acid of formula $Q^1$-COOH or an acid halide of formula $Q^1$-CO-Hal, wherein Hal is Cl, F or Br, under standard conditions as described in 1).

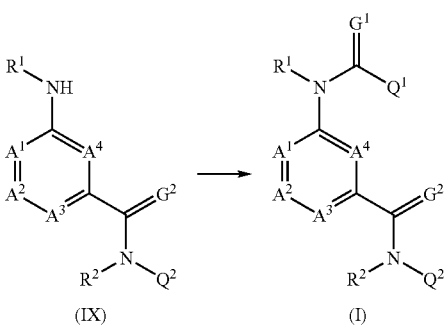

10) Compounds of formula (IX), wherein $G^2$ is oxygen, may be formed from compounds of formula (VI), wherein P is a suitable protecting group and R is OH, Cl or $C_1$-$C_6$alkoxy, by amide bond formation with an amine of formula $NHR^2Q^2$ under standard conditions as described in 1), followed by removal of the protecting group P under standard conditions.

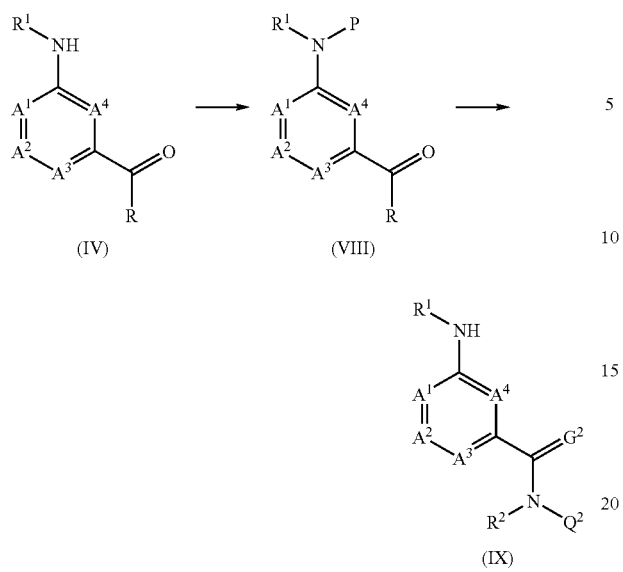

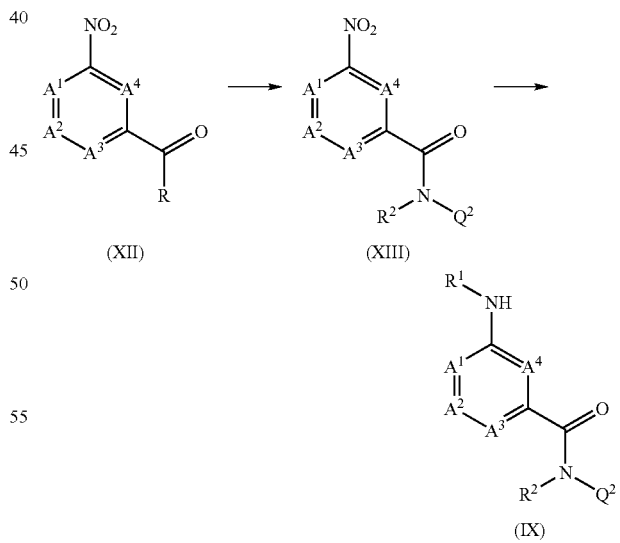

11) Compounds of formula (VIII), wherein R is OH or $C_1$-$C_6$alkoxy, may be made by the protection of the amine functionality in compounds of formula (IV), wherein R is OH or $C_1$-$C_6$alkoxy. Suitable protecting groups include carbamates (such as tert-butyloxycarbonyl, allyloxycarbonyl and benzyloxycarbonyl), trialkylsilyl groups (such as tert-butyldimethyl-silyl) and acyl groups (such as acetyl). The formation and removal of such groups is widely reported in the literature and is known to a person skilled in the art.

12) For compounds of formula (VIII) and compounds of formula (IV), the esters (wherein R is $C_1$-$C_6$alkoxy) may be hydrolysed to the acids (wherein R is OH) by treatment with an alkali hydroxide, such as sodium hydroxide, in a solvent, such as ethanol. The acids (wherein R is OH) may be converted to the acid chlorides (wherein R is Cl) by treatment with thionyl chloride or oxalyl chloride as described in 2) and 3).

13) Alternatively, it may be possible to convert compounds of formula (IV), wherein R is OH, Cl, F, Br or $C_1$-$C_6$alkoxy, directly to compounds of formula (IX) by amide bond formation with an amine of formula $NHR^2Q^2$ under standard conditions as described in 1).

14) Alternatively, compounds of formula (IX), wherein $G^2$ is oxygen, may be made from compounds of formula (XI), wherein $G^2$ is oxygen and LG is a leaving group such as fluoro, chloro or sulfonate, by displacement of the leaving group with a compound of formula $R^1$—$NH_2$. Such reactions are usually performed under basic conditions.

15) Compounds of formula (XI) may be made from compounds of formula (X), wherein R is Cl or OH and LG is a leaving group as described in 14), via amide bond formation under standard conditions as described in 1). Compounds of formula (X) and formula (IV) are either known compounds or may be made by methods known to the person skilled in the art.

16) Compounds of formula (I), wherein $G^1$ is oxygen and $G^2$ is sulfur, may be made by treatment of compounds of formula (XI), wherein $G^2$ is oxygen and LG is a leaving group, or compounds of formula (IX), wherein $G^2$ is oxygen, with a thio-transfer reagent such as Lawesson's reagent or phosphorus pentasulfide prior to elaborating to compounds of formula (I), wherein $G^1$ is oxygen and $G^2$ is sulfur, as described in 9).

17) An alternative synthesis of compounds of formula (IX), wherein $R^1$ is hydrogen, may be achieved by the reduction of nitro compounds of formula (XIII). There are numerous methods for achieving such a transformation reported in the literature such as treatment with tin chloride under acidic conditions, or hydrogenation catalysed by a noble metal such as palladium on carbon.

18) Compounds of formula (XIII) may be derived from compounds of formula (XII), wherein R is OH, Cl, or $C_1$-$C_6$alkoxy, via acylation with an amine of formula $NHR^2Q^2$ under the standard conditions as described in 1).

19) For compounds of formula (XII), the esters (wherein R is $C_1$-$C_6$alkoxy) may be hydrolysed to the acids (wherein R is OH) by treatment with an alkali hydroxide, such as sodium hydroxide, in a solvent, such as ethanol as described in 3). The acids (wherein R is OH) may be converted to the acid chlorides (wherein R is Cl) by treatment with thionyl chloride or oxalyl chloride as described in 2). Compounds of formula (XII) are either known or may be made by methods known to a person skilled in the art.

20) Compounds of formula (XII) wherein X is oxygen and $R^3$ is as defined above, can be made from a compound of formula (XII) wherein LG is halogen, such as fluorine or chlorine, by reaction with the corresponding alcohol in the presence of a base, such as NaH for an aliphatic alcohol or benzylic alcohol and NaH for a phenol or a heteroaromatic alcohol.

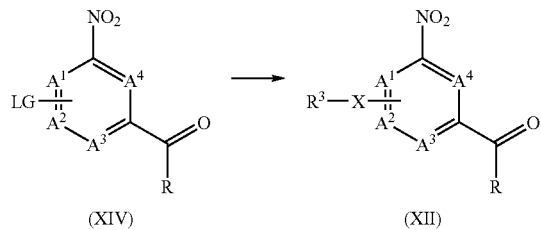

The displacement of a halogen with an oxygen nucleophile can also be carried out on intermediates of formula (XIII).

21) Compounds of formula (XII) wherein X is sulfur and $R^3$ is as defined above, can be made from a compound of formula (XII) wherein LG is halogen, such as fluorine or chlorine, by reaction with the corresponding thiol in the presence of a base, such as NaH for an aliphatic thiol or benzylic thiol and NaH for an aromatic thiol or a heteroaromatic thiol. The displacement of a halogen with a sulfur nucleophile can also be carried out on intermediates of formula (XIII).

22) Compounds of formula (XII) wherein X is N—$R^4$ and $R^3$ and $R^4$ are as defined above can be made from a compound of formula (XII) wherein LG is halogen, such as fluorine or chlorine, by reaction with the corresponding amine optionally in the presence of a base. The displacement of a halogen with a nitrogen nucleophile can also be carried out on intermediates of formula (XIII).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures preferably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)- 2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen; or s) Flubendiamid or rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of
5-(3-chloro-benzoylamino)-2-phenoxy-benzoic acid methyl ester

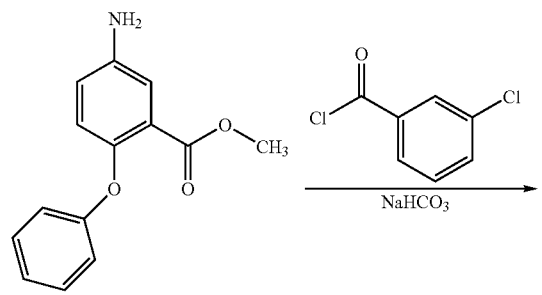

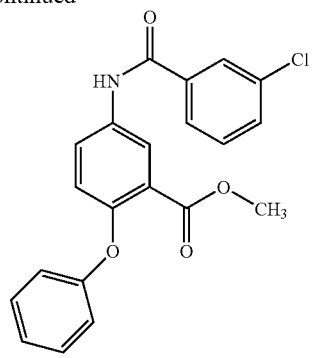

5-Amino-2-phenoxy-benzoic acid methyl ester (972 mg, 4.00 mmol) (prepared according to WO 01/046171) was dissolved in a biphasic mixture of ethyl acetate (10 ml) and aqueous sodium bicarbonate (1N) (10 ml). 3-Chloro-benzoylchloride (770 µl, 6 mmol) was added under vigorous stirring. The mixture was stirred for 18 hours at ambient temperature. The phases were separated, the organic phase was dried over sodium sulfate and concentrated. The residue was used without further purification.

Example I2

Preparation of
5-(3-chloro-benzoylamino)-2-phenoxy-benzoic acid

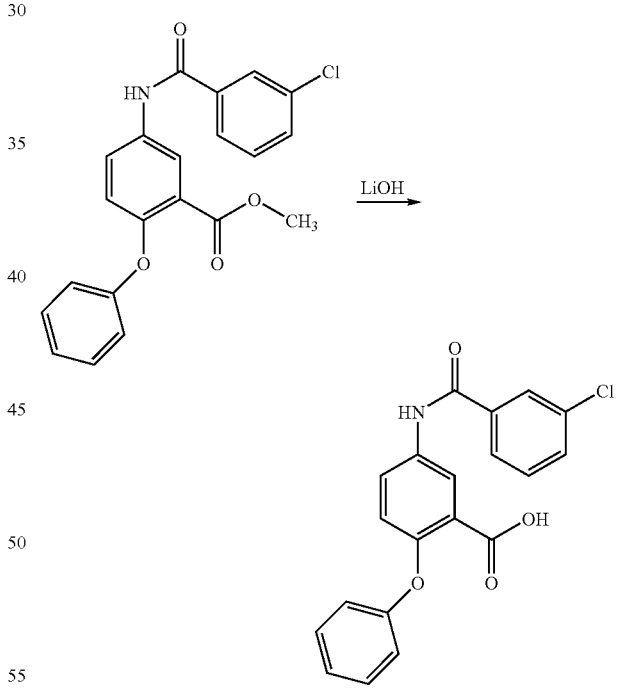

5-(3-Chloro-benzoylamino)-2-phenoxy-benzoic acid methyl ester (1.56 g, 4.00 mmol) (see Example I1) was dissolved in a mixture of tetrahydrofuran (15 ml), methanol (1.5 ml), and water (1.5 ml). Lithium hydroxide monohydrate (336 mg, 8 mmol) was added and the reaction mixture stirred at ambient temperature for 3 days. The reaction mixture was concentrated and the residue extracted with water and tert-butyl-methyl-ether. The aqueous phase was acidified by the addition of a few drops of concentrated hydrochloric acid and extracted with ethyl acetate. The phases were separated, the organic phase was dried over sodium sulfate and concentrated. The residue was used without further purification.

Example P1

Preparation of 5-(3-chloro-benzoylamino)-N-[2,6-dimethyl-4-(1,2,2,2-tetrafluoro-1-trifluoromethyl-ethyl)-phenyl]-2-phenoxy-benzamide

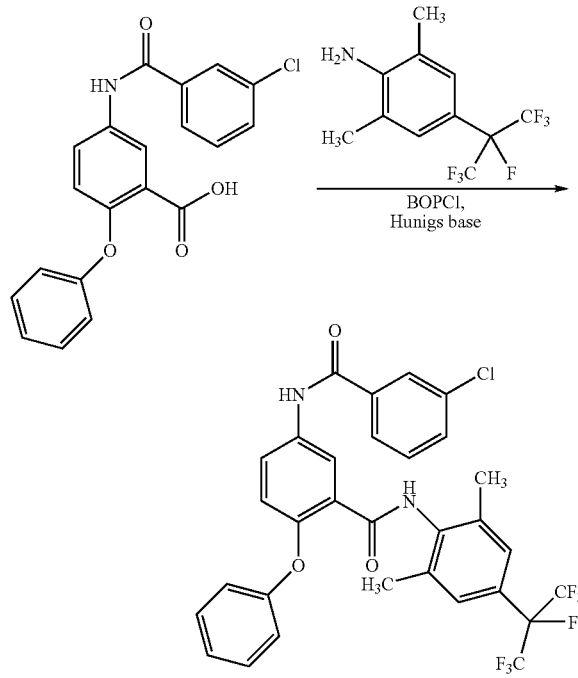

5-(3-Chloro-benzoylamino)-2-phenoxy-benzoic acid (200 mg, 0.54 mmol) (see Example I2) was suspended in dichloromethane (2 ml), followed by the addition of bis(2-oxo-3-oxazolidinyl)phosphonic chloride "BOP-Cl" (208 mg, 0.81 mmol), diisopropyl-ethylamine "Hunigs base" (280 μl, 1.63 mmol) and 2,6-dimethyl-4-(1,2,2,2-tetrafluoro-1-trifluoromethyl-ethyl)-aniline (158 mg, 0.54 mmol) (=4-heptafluoroisopropyl-2,6-dimethylaniline, prepared according to US 2002/198399). The reaction mixture was stirred for 18 hours at ambient temperature, followed by extraction with aqueous sodium bicarbonate (1N) and dichloromethane. The organic phase was washed successively with aqueous hydrochloric acid (2N) and aqueous sodium bicarbonate (1N), dried over sodium sulfate and concentrated. The residue was purified by preparative reverse phase chromatography to yield Compound No. A1 of Table A below (113 mg, 32% yield over three steps).

Example I3

Preparation of N-[2,6-dimethyl-4-(1,2,2,2-tetrafluoro-1-trifluoromethyl-ethyl)-phenyl]-2,6-dimethoxy-3-nitrobenzamide

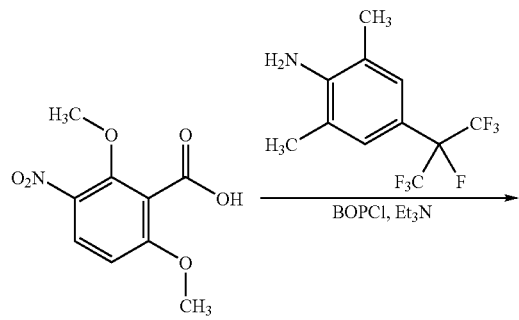

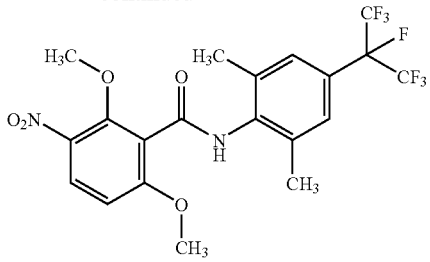

To a solution of 2,6-dimethyl-4-(1,2,2,2-tetrafluoro-1-trifluoromethyl-ethyl)-aniline (145 mg, 0.5 mmol) and 2,6-dimethoxy-3-nitrobenzoic acid (136 mg, 0.6 mmol) in dichloromethane (10 ml) was added triethylamine (210 μl, 1.5 mmol) and bis(2-oxo-3-oxazolidinyl)phosphonic chloride "BOP-Cl" (153 mg, 0.6 mmol). The reaction mixture was heated to reflux for 48 hours. The reaction mixture was cooled to ambient temperature and quenched by the addition of a saturated sodium bicarbonate solution (10 ml). The phases were separated, the organic phase was dried over sodium sulfate and concentrated. Purification by chromatography over silica gel (eluent: hexane/ethyl acetate 2:1) gave N-[2,6-dimethyl-4-(1,2,2,2-tetrafluoro-1-trifluoromethyl-ethyl)-phenyl]-2,6-dimethoxy-3-nitrobenzamide (222 mg, 89% yield).

Example I4

Preparation of N-[2,6-dimethyl-4-(1,2,2,2-tetrafluoro-1-trifluoromethyl-ethyl)-phenyl]-2-fluoro-5-nitrobenzamide

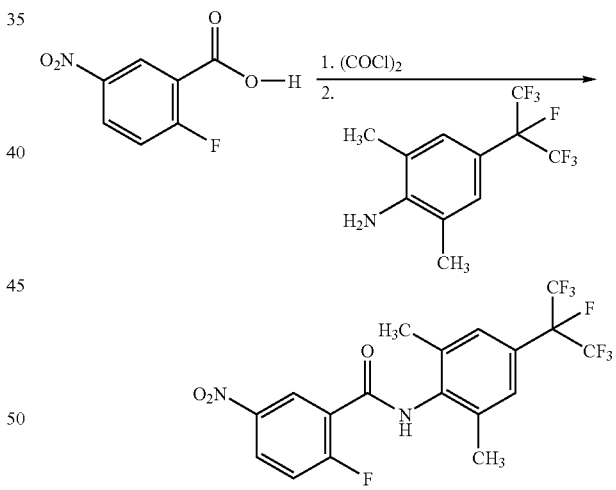

To a suspension of 2-fluoro-5-nitrobenzoic acid (10 g, 54 mmol) in dichloromethane (80 ml) was added oxalyl chloride (5.5 ml, 64.8 mmol) at ambient temperature, then two drops of N,N-dimethylformamide were added. The mixture was stirred for 1 hour at ambient temperature then heated to reflux for 3 hours. The solvents and volatile products were removed under vacuum and the residue was suspended in tetrahydrofuran (30 ml). 4-Heptafluoroisopropyl-2,6-dimethylaniline (12.5 g, 43.2 mmol) was dissolved in tetrahydro-furan (60 ml) and pyridine (8.7 ml, 108 mmol) was added. The mixture was cooled to 0° C. and the solution of 2-fluoro-5-nitrobenzoyl chloride was added. The mixture was stirred at room temperature for 12 hours. Then saturated aqueous sodium bicarbonate (100 ml) was added and the organic phase extracted twice with ethyl acetate (2×200 ml). The combined organic extracts were dried over sodium sulfate and concentrated. The residue was purified by chromatography on silica gel (eluent:cyclohexane/ethyl acetate ratio 1:4), yielding N-[2,6-dimethyl-4-(1,2,2,2-tetrafluoro-1-trifluoromethyl-ethyl)-phenyl]-2-fluoro-5-nitrobenzamide (19 g, 96% yield). $^1$H-NMR (CDCl$_3$, 400 MHz): 9.8 (m, 1H), 8.5 (m, 2H), 7.9 (d, 1H), 7.45 (t, 1H), 7.4 (s, 2H), 2.4 (s, 6H).

Example I5

Preparation of N-[2,6-dimethyl-4-(1,2,2,2-tetrafluoro-1-trifluoromethyl-ethyl)-phenyl]-2-ethylamino-5-nitrobenzamide

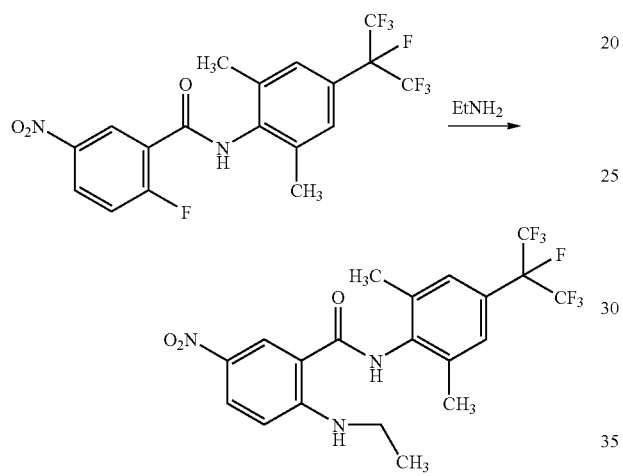

To a solution of N-[2,6-dimethyl-4-(1,2,2,2-tetrafluoro-1-trifluoromethyl-ethyl)-phenyl]-2-fluoro-5-nitrobenzamide (5.0 g, 11 mmol) (see Example I4) in acetonitrile (100 ml) was added a solution of N-ethylamine in water (70% by weight) (2.23 ml, 28 mmol). The reaction mixture was stirred at ambient temperature for 30 minutes. The reaction mixture was concentrated and the residue purified by chromatography over silica gel (eluent: ethyl acetate) to give N-[2,6-dimethyl-4-(1,2,2,2-tetrafluoro-1-trifluoromethyl-ethyl)-phenyl]-2-ethylamino-5-nitrobenzamide (4.8 g, 91% yield).

Example I6

Preparation of 4-dimethylamino-N-[2,6-dimethyl-4-(1,2,2,2-tetrafluoro-1-trifluoromethyl-ethyl)-phenyl]-3-nitrobenzamide

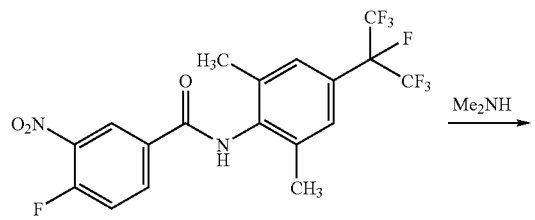

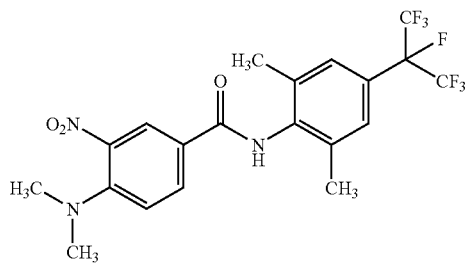

To a solution of N-[2,6-dimethyl-4-(1,2,2,2-tetrafluoro-1-trifluoromethyl-ethyl)-phenyl]-4-fluoro-3-nitrobenzamide (5.0 g, 11 mmol) (prepared according to WO 05/073165) in acetonitrile (100 ml) was added a solution of N,N-dimethylamine in water (40% by weight) (3.55 ml, 28 mmol). The reaction mixture was stirred at ambient temperature for 30 minutes. Then the reaction mixture was concentrated and the residue purified by chromatography over silica gel (eluent: ethyl acetate) to give 4-dimethylamino-N-[2,6-dimethyl-4-(1,2,2,2-tetrafluoro-1-trifluoromethyl-ethyl)-phenyl]-3-nitrobenzamide (5.3 g, 100% yield).

Example I7

Preparation of 3-amino-N-[2,6-dimethyl-4-(1,2,2,2-tetrafluoro-1-trifluoromethyl-ethyl)-phenyl]-2,6-dimethoxy-benzamide

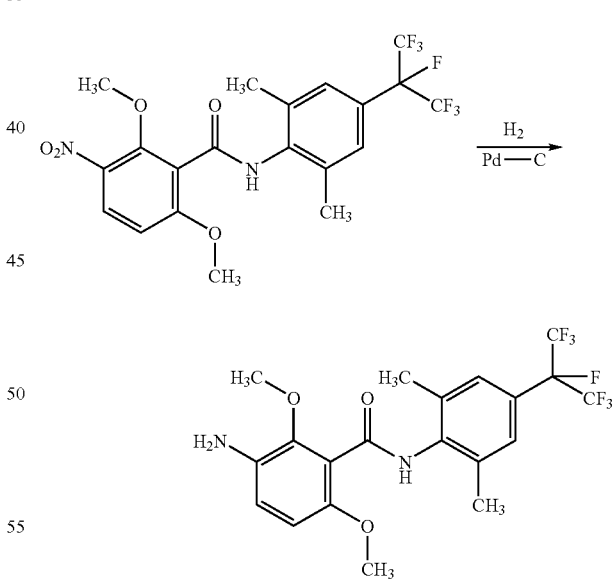

A solution of N-[2,6-dimethyl-4-(1,2,2,2-tetrafluoro-1-trifluoromethyl-ethyl)-phenyl]-2,6-dimethoxy-3-nitrobenzamide (200 mg, 0.4 mmol) (see Example I3) in ethanol (8 ml) charged with Pd/C 10% (64 mg, 0.06 mmol) was stirred under a hydrogen atmosphere for 16 hours. After filtration the mixture was concentrated. The residue was used without further purification.

Example I8

Preparation of 5-amino-N-[2,6-dimethyl-4-(1,2,2,2-tetrafluoro-1-trifluoromethyl-ethyl)-phenyl]-2-ethylamino-benzamide

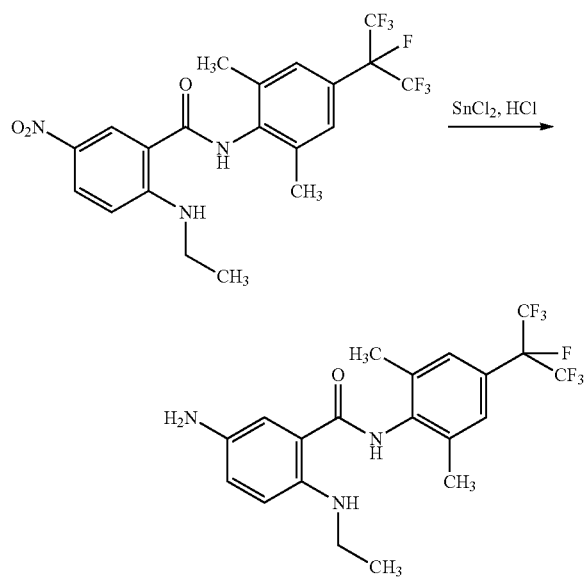

N-[2,6-dimethyl-4-(1,2,2,2-tetrafluoro-1-trifluoromethyl-ethyl)-phenyl]-2-ethylamino-5-nitrobenzamide (3.0 g, 6.2 mmol) (see Example I5) was dissolved in isopropanol (50 ml) and tin chloride (4.2 g, 22.3 mmol) was added. The mixture was cooled to 0° C. and a solution of concentrated hydrogen chloride (6 ml) was added slowly. The reaction mixture was stirred at 80° C. for 2 hours. Then ⅓ of the total volume of isopropanol was evaporated. Water (100 ml) was added to the concentrated mixture and a solution of aqueous sodium hydroxide (4N) to adjust the pH to 7-8. The aqueous phase was extracted three times with ethyl acetate (200 ml). The combined organic extracts were dried over sodium sulfate and concentrated. The residue was used without further purification (2.8 g, 100% yield).

Example I9

Preparation of 3-amino-4-dimethylamino-N-[2,6-dimethyl-4-(1,2,2,2-tetrafluoro-1-trifluoromethyl-ethyl)-phenyl]-benzamide

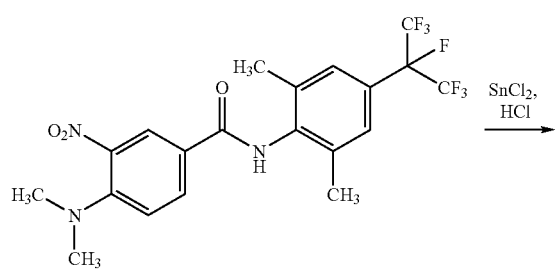

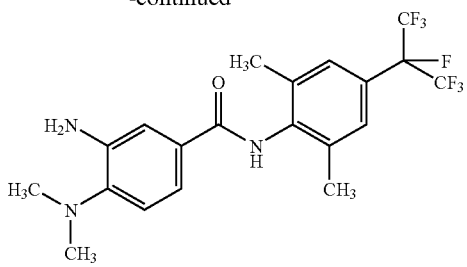

4-Dimethylamino-N-[2,6-dimethyl-4-(1,2,2,2-tetrafluoro-1-trifluoromethyl-ethyl)-phenyl]-3-nitrobenzamide (3.0 g, 6.2 mmol) (see Example I6) was dissolved in isopropanol (50 ml) and tin chloride (4.2 g, 22.3 mmol) was added. The mixture was cooled to 0° C. and a solution of concentrated hydrogen chloride (6 ml) was added slowly. The reaction mixture was stirred at 80° C. for 2 hours. Then ⅓ of the total volume of isopropanol was evaporated. Water (100 ml) was added to the concentrated mixture and a solution of aqueous sodium hydroxide (4N) to adjust the pH to 7-8. The aqueous phase was extracted three times with ethyl acetate (200 ml). The combined organic extracts were dried over sodium sulfate and concentrated. The residue was used without further purification (2.7 g, 96% yield).

Example P2

Preparation of N-[2,6-dimethyl-4-(1,2,2,2-tetrafluoro-1-trifluoromethyl-ethyl-phenyl]-3-(4-fluoro-benzoylamino)-2,6-dimethoxy-benzamide

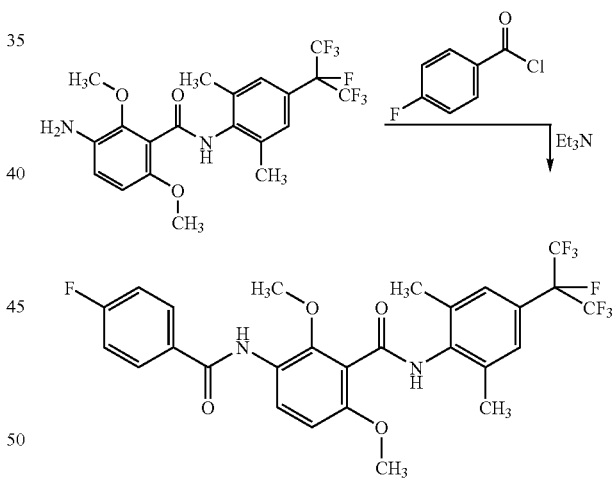

To a solution of 3-amino-N-[2,6-dimethyl-4-(1,2,2,2-tetrafluoro-1-trifluoromethyl-ethyl)-phenyl]-2,6-dimethoxy-benzamide (80 mg, 0.17 mmol) (see Example I7) in dichloromethane (2 ml) was added triethylamine (71 µl, 0.51 mmol) and α-fluorobenzoyl chloride (24.2 µl, 0.20 mmol). The reaction mixture was heated to reflux for 15 hours. The reaction mixture was cooled to ambient temperature and quenched by addition of saturated aqueous sodium bicarbonate (5 ml). The phases were separated and the aqueous phase was extracted with dichloromethane (2×5 ml). The combined organic phases were dried over sodium sulfate and concentrated. Purification by chromatography over silica gel (eluent:hexane/ethyl acetate ratio 3:1) gave Compound No. A9 of Table A below (56 mg, 56% yield).

Example P3

Preparation of 5-(4-cyano-benzoylamino)-N-[2,6-dimethyl-4-(1,2,2,2-tetrafluoro-1-trifluoromethyl-ethyl)-phenyl]-2-ethylamino-benzamide

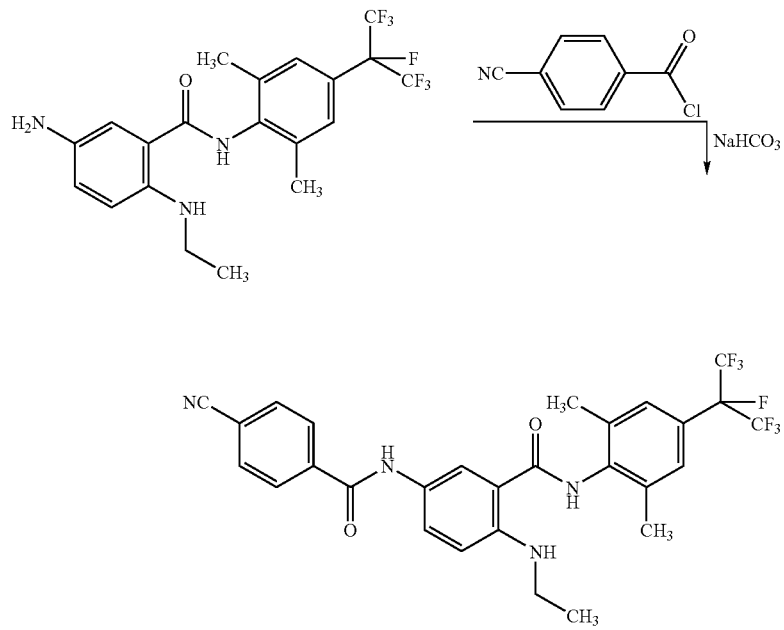

N-[2,6-dimethyl-4-(1,2,2,2-tetrafluoro-1-trifluoromethyl-ethyl)-phenyl]-2-ethylamino-benzamide (200 mg, 0.44 mmol) (see Example I8) was dissolved in a biphasic mixture of ethyl acetate (4 ml) and aqueous sodium bicarbonate (1N) (4 ml). 4-Cyano-benzoyl-chloride (75 mg, 0.44 mmol) was added under vigorous stirring. The mixture was stirred for 18 hours at ambient temperature. The phases were separated, the organic phase was dried over sodium sulfate and concentrated. Purification by chromatography over silica gel (eluent: cyclohexane/ethyl acetate ratio 1:1) gave Compound No. A15 of Table A below (0.12 g, 47% yield).

Example P4

Preparation of 3-(4-Cyano-benzoylamino)-4-dimethylamino-N-[2,6-dimethyl-4-(1,2,2,2-tetrafluoro-1-trifluoromethyl-ethyl)-phenyl]-benzamide

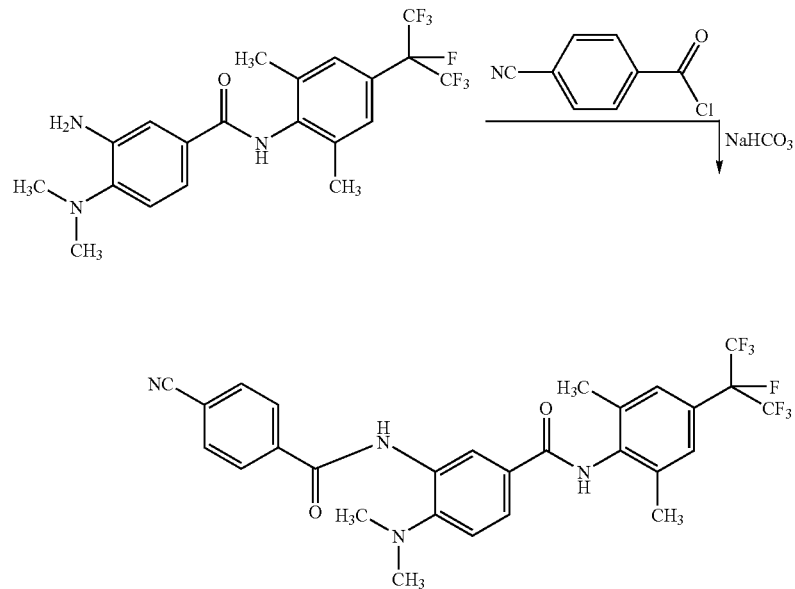

3-Amino-4-dimethylamino-N-[2,6-dimethyl-4-(1,2,2,2-tetrafluoro-1-trifluoromethyl-ethyl)-phenyl]-benzamide (200 mg, 0.44 mmol) (see Example I9) was dissolved in a biphasic mixture of ethyl acetate (4 ml) and aqueous sodium bicarbonate (1N) (4 ml). 4-Cyano-benzoyl chloride (75 mg, 0.44 mmol) was added under vigorous stirring. The reaction mixture was stirred for 18 hours at ambient temperature. The phases were separated, the organic phase was dried over sodium sulfate and concentrated. Purification by chromatography over silica gel (eluent:cyclohexane/ethyl acetate ratio 1:1) gave Compound No. A16 of Table A below (244 mg, 95% yield).

The following method was used for HPLC-MS analysis for A1 to A18 and A108 to A111:

Method (Agilent 1100 LC) with the following HPLC gradient conditions (Solvent A: 0.05% of formic acid in water and Solvent B: 0.04% of formic acid in acetonitrile)

| Time (minutes) | A (%) | B (%) | Flow rate (ml/min) |
|---|---|---|---|
| 0 | 95 | 5 | 1.7 |
| 2.0 | 0 | 100 | 1.7 |
| 2.8 | 0 | 100 | 1.7 |
| 2.9 | 95 | 5 | 1.7 |
| 3.1 | 95 | 5 | 1.7 |

Type of column: Phenomenex Gemini C18; Column length: 30 mm; Internal diameter of column: 3 mm; Particle Size: 3 micron; Temperature: 60° C.

The following method was used for HPLC-MS analysis for A19 to A107: Method (Water Alliance 2795 LC) with the following HPLC gradient conditions (Solvent A: 0.1% of formic acid in water/acetonitrile (9:1) and Solvent B: 0.1% of formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.

The characteristic values obtained for each compound were the retention time ("RT" recorded in minutes) and the molecular ion, typically the cation MH+, as listed in the following tables.

TABLE A

Compounds of formula (If):

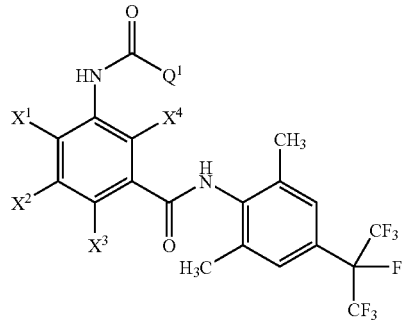

(If)

| Compound No. | $Q^1$ | $X^1$ | $X^2$ | $X^3$ | $X^4$ | RT (min) | MH+ |
|---|---|---|---|---|---|---|---|
| A1 | 3-chloro-phenyl | H | H | PhO— | H | 2.31 | 639 |
| A2 | 3-chloro-phenyl | MeS— | H | H | H | 2.18 | 593 |
| A3 | 3-chloro-phenyl | H | H | PhS— | H | 2.30 | 655 |
| A4 | 3-chloro-phenyl | H | H | p-Me-PhS— | H | 2.34 | 669 |
| A5 | 3-chloro-phenyl | m-Me-PhO— | H | H | H | 2.33 | 653 |
| A6 | 3-chloro-phenyl | p-Cl—PhO— | H | H | H | 2.32 | 673 |
| A7 | 4-cyano-phenyl | H | H | H | HO— | 2.11 | 594 |
| A8 | 4-cyano-phenyl | H | H | H | allyl-O— | 2.18 | 554 |
| A9 | 4-fluoro-phenyl | H | MeO— | H | MeO— | 2.18 | 591 |
| A10 | 4-fluoro-phenyl | MeO— | H | H | H | 2.14 | 561 |

TABLE A-continued

Compounds of formula (If):

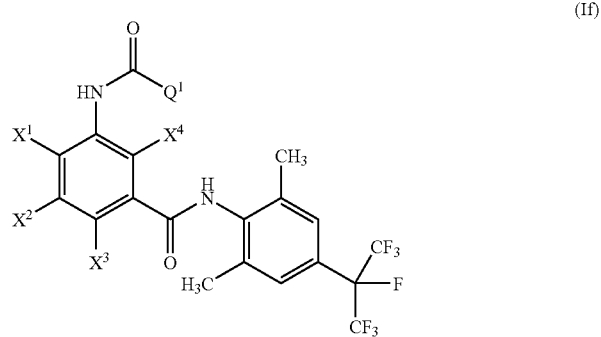

(If)

| Compound No. | $Q^1$ | $X^1$ | $X^2$ | $X^3$ | $X^4$ | RT (min) | MH+ |
|---|---|---|---|---|---|---|---|
| A11 | 4-fluoro-phenyl | H | H | MeO— | MeO— | 2.08 | 591 |
| A12 | 4-fluoro-phenyl | H | H | MeO— | H | 2.16 | 561 |
| A13 | 4-fluoro-phenyl | H | H | EtO— | H | 2.20 | 575 |
| A14 | 4-fluoro-phenyl | H | H | n-Pr—O— | H | 2.24 | 589 |
| A15 | 4-cyano-phenyl | H | H | EtHN— | H | 2.17 | 581 |
| A16 | 4-cyano-phenyl | Me$_2$N— | H | H | H | 2.12 | 581 |
| A17 | 4-cyano-phenyl | H | H | Me$_2$N— | H | 2.17 | 581 |
| A18 | 4-cyano-phenyl | EtHN— | H | H | H | 2.04 | 581 |
| A19 | 2-chloro-pyrid-3-yl | H | H | Me$_2$N— | H | 1.87 | 591 |
| A20 | 2-fluoro-pyrid-3-yl | H | H | Me$_2$N— | H | 1.9 | 575 |
| A22 | 3-chloro-phenyl | H | H | Me$_2$N— | H | 2.2 | 590 |
| A23 | 2-chloro-phenyl | H | H | Me$_2$N— | H | 2 | 590 |
| A24 | 2-chloro-pyrid-4-yl | H | H | Me$_2$N— | H | 2 | 591 |
| A25 | 5-bromo-furan-2-yl | H | H | Me$_2$N— | H | 2 | 624 |
| A26 | 2-bromo-phenyl | H | H | Me$_2$N— | H | 2.05 | 634 |
| A27 | 3-chloro-5-trifluoromethyl-pyrid-2-yl | H | H | Me$_2$N— | H | 2.19 | 659 |
| A28 | 2-methylthio-pyrid-3-yl | H | H | Me$_2$N— | H | 1.97 | 603 |
| A29 | 2-fluoro-3-trifluoromethyl-phenyl | H | H | Me$_2$N— | H | 2.2 | 641 |
| A30 | 2,5-dichloro-phenyl | H | H | Me$_2$N— | H | 2.18 | 624 |
| A31 | 6-chloro-pyrid-3-yl | H | H | Me$_2$N— | H | 1.97 | 591 |
| A32 | 4-nitro-phenyl | H | H | Me$_2$N— | H | 2.1 | 601 |
| A33 | 4-fluoro-phenyl | H | H | Me$_2$N— | H | 2 | 574 |
| A34 | phenyl | H | H | Me$_2$N— | H | 2 | 556.2 |
| A35 | 2,3-difluoro-phenyl | H | H | Me$_2$N— | H | 2 | 556.2 |
| A36 | 5-chloro-thiophen-2-yl | H | H | Me$_2$N— | H | 2.18 | 596.1 |
| A37 | 1,2,3-thiadiazol-4-yl | H | H | Me$_2$N— | H | 1.9 | 564.1 |
| A38 | 1,3-dimethyl-pyrazol-5-yl | H | H | Me$_2$N— | H | 1.9 | 574.2 |
| A39 | 3-methyl-pyrid-2-yl | H | H | Me$_2$N— | H | 2.1 | 571.2 |

TABLE A-continued

Compounds of formula (If):

(If)

| Compound No. | Q¹ | X¹ | X² | X³ | X⁴ | RT (min) | MH⁺ |
|---|---|---|---|---|---|---|---|
| A40 | 2-methyl-phenyl | H | H | Me₂N— | H | 2 | 570.2 |
| A41 | 2-chloro-pyrid-3-yl | Me₂N— | H | H | H | 1.9 | 591.1 |
| A42 | 2-fluoro-pyrid-3-yl | Me₂N— | H | H | H | 2.0 | 575.2 |
| A44 | 3-chloro-phenyl | Me₂N— | H | H | H | 2.2 | 590.1 |
| A45 | 2-chloro-phenyl | Me₂N— | H | H | H | 2.1 | 590.1 |
| A46 | 2-chloro-pyrid-4-yl | Me₂N— | H | H | H | 2 | 591.1 |
| A47 | 5-bromo-pyrid-3-yl | Me₂N— | H | H | H | 1.98 | 635.1 |
| A48 | 5-bromo-furan-2-yl | Me₂N— | H | H | H | 2.1 | 624.1 |
| A49 | 2-bromo-phenyl | Me₂N— | H | H | H | 2.1 | 634.1 |
| A50 | 3-chloro-5-trifluoromethyl-pyrid-2-yl | Me₂N— | H | H | H | 2.3 | 659.1 |
| A51 | 2-methylthio-pyrid-3-yl | Me₂N— | H | H | H | 2 | 603.2 |
| A52 | 2-fluoro-3-trifluoromethyl-phenyl | Me₂N— | H | H | H | 2.3 | 642.2 |
| A53 | 2,5-dichloro-phenyl | Me₂N— | H | H | H | 2.2 | 624.1 |
| A54 | 6-chloro-pyrid-3-yl | Me₂N— | H | H | H | 2 | 591.1 |
| A55 | 4-nitro-phenyl | Me₂N— | H | H | H | 2.1 | 601.2 |
| A56 | 4-fluoro-phenyl | Me₂N— | H | H | H | 2.1 | 574.2 |
| A57 | phenyl | Me₂N— | H | H | H | 2.1 | 556.2 |
| A58 | 2,3-difluoro-phenyl | Me₂N— | H | H | H | 2.2 | 592.2 |
| A59 | 5-chloro-thiophen-2-yl | Me₂N— | H | H | H | 2.2 | 596.1 |
| A60 | 1,2,3-thiadiazol-4-yl | Me₂N— | H | H | H | 2.0 | 564.1 |
| A61 | 1,3-dimethyl-pyrazol-5-yl | Me₂N— | H | H | H | 1.9 | 574.2 |
| A62 | 2-methyl-phenyl | Me₂N— | H | H | H | 2.1 | 570.2 |
| A63 | 2-chloro-pyrid-3-yl | H | H | EtHN— | H | 2 | 591.1 |
| A64 | 2-fluoro-pyrid-3-yl | H | H | EtHN— | H | 1.99 | 575.2 |
| A66 | 3-chloro-phenyl | H | H | EtHN— | H | 2.21 | 590.1 |
| A67 | 2-chloro-phenyl | H | H | EtHN— | H | 2.11 | 590.1 |
| A68 | 2-chloro-pyrid-4-yl | H | H | EtHN— | H | 2.08 | 591.1 |

TABLE A-continued

Compounds of formula (If):

(If)

| Compound No. | Q¹ | X¹ | X² | X³ | X⁴ | RT (min) | MH⁺ |
|---|---|---|---|---|---|---|---|
| A69 | 5-bromo-pyrid-3-yl | H | H | EtHN— | H | 2.09 | 634.1 |
| A70 | 5-bromo-furan-2-yl | H | H | EtHN— | H | 2.2 | 624.1 |
| A71 | 2-bromo-phenyl | H | H | EtHN— | H | 2.12 | 634.1 |
| A72 | 3-chloro-5-trifluoromethyl-pyrid-2-yl | H | H | EtHN— | H | 2.27 | 659.1 |
| A73 | 2-methylthio-pyrid-3-yl | H | H | EtHN— | H | 2.1 | 603.2 |
| A74 | 2-fluoro-3-trifluoromethyl-phenyl | H | H | EtHN— | H | 2.26 | 642.2 |
| A75 | 2,5-dichloro-phenyl | H | H | EtHN— | H | 2.2 | 624.1 |
| A76 | 6-chloro-pyrid-3-yl | H | H | EtHN— | H | 2.1 | 591.1 |
| A77 | 4-nitro-phenyl | H | H | EtHN— | H | 2.1 | 602.1 |
| A78 | 4-fluoro-phenyl | H | H | EtHN— | H | 2.1 | 574.2 |
| A79 | phenyl | H | H | EtHN— | H | 2.1 | 556.2 |
| A80 | 2,3-difluoro-phenyl | H | H | EtHN— | H | 2.2 | 592.2 |
| A81 | 5-chloro-thiophen-2-yl | H | H | EtHN— | H | 2.2 | 596.1 |
| A82 | 1,2,3-thiadiazol-4-yl | H | H | EtHN— | H | 2 | 564.1 |
| A83 | 1,3-dimethyl-pyrazol-5-yl | H | H | EtHN— | H | 2 | 574.2 |
| A84 | 2-methyl-phenyl | H | H | EtHN— | H | 2.1 | 570.2 |
| A85 | 3-methyl-pyrid-2-yl | H | H | EtHN— | H | 2.2 | 570.2 |
| A86 | 2-chloro-pyrid-3-yl | EtHN— | H | H | H | 1.8 | 591.1 |
| A87 | 2-fluoro-pyrid-3-yl | EtHN— | H | H | H | 1.8 | 575.2 |
| A89 | 3-chloro-phenyl | EtHN— | H | H | H | 2.01 | 590.1 |
| A90 | 2-chloro-phenyl | EtHN— | H | H | H | 1.9 | 590.1 |
| A91 | 2-chloro-pyrid-4-yl | EtHN— | H | H | H | 1.9 | 591.1 |
| A92 | 5-bromo-pyrid-3-yl | EtHN— | H | H | H | 1.9 | 635.1 |
| A93 | 5-bromo-furan-2-yl | EtHN— | H | H | H | 1.9 | 624.1 |
| A94 | 2-bromo-phenyl | EtHN— | H | H | H | 1.9 | 634.1 |

TABLE A-continued

Compounds of formula (If):

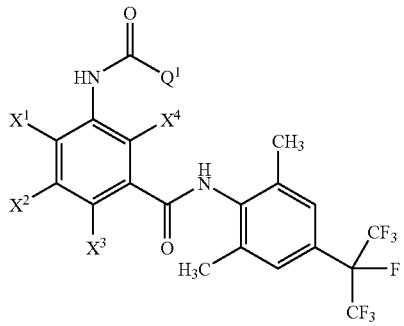

(If)

| Compound No. | Q¹ | X¹ | X² | X³ | X⁴ | RT (min) | MH⁺ |
|---|---|---|---|---|---|---|---|
| A95 | 3-chloro-5-trifluoromethyl-pyrid-2-yl | EtHN— | H | H | H | 2 | 659.1 |
| A96 | 2-methylthio-pyrid-3-yl | EtHN— | H | H | H | 1.9 | 603.2 |
| A97 | 2-fluoro-3-trifluoromethyl-phenyl | EtHN— | H | H | H | 2.1 | 641.2 |
| A98 | 2,5-dichloro-phenyl | EtHN— | H | H | H | 2 | 624.1 |
| A99 | 6-chloro-pyrid-3-yl | EtHN— | H | H | H | 1.84 | 591.1 |
| A100 | 4-nitro-phenyl | EtHN— | H | H | H | 1.9 | 601.2 |
| A101 | 4-fluoro-phenyl | EtHN— | H | H | H | 1.9 | 574.2 |
| A102 | phenyl | EtHN— | H | H | H | 1.9 | 555.2 |
| A103 | 2,3-difluoro-phenyl | EtHN— | H | H | H | 2 | 592.2 |
| A104 | 5-chloro-thiophen-2-yl | EtHN— | H | H | H | 2 | 596.1 |
| A105 | 1,2,3-thiadiazol-4-yl | EtHN— | H | H | H | 1.78 | 564.1 |
| A106 | 1,3-dimethyl-pyrazol-5-yl | EtHN— | H | H | H | 1.8 | 574.2 |
| A107 | 2-methyl-phenyl | EtHN— | H | H | H | 1.9 | 571.2 |
| A108 | 2-chloro-5-nitro-phenyl | allyl-O— | H | H | H | 2.18 | 648 |
| A109 | 2-chloro-5-nitro-phenyl | HO— | H | H | H | 2.04 | 608 |
| A110 | 4-fluoro-phenyl | HO— | H | H | H | 2.04 | 547 |
| A111 | 2,6-dichloro-pyrid-3-yl | HO— | H | H | H | 2.06 | 599 |
| A112 | 4-fluoro-phenyl | H | MeO— | H | H | 2.14 | 561 |
| A113 | 4-fluoro-phenyl | H | H₂N— | H | H | 2.01 | 547 |

TABLE B

Compounds of formula (Ig):

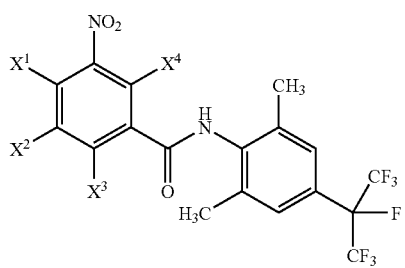

(Ig)

| Compound No. | $X^1$ | $X^2$ | $X^3$ | $X^4$ | RT (min) | $MH^+$ |
|---|---|---|---|---|---|---|
| B1 | H | MeO— | H | MeO— | 2.16 | 499 |
| B2 | MeO— | H | H | H | 2.06 | 469 |
| B3 | H | H | MeO— | MeO— | 2.04 | 499 |
| B4 | H | H | MeO— | H | 2.09 | 469 |
| B5 | H | H | OEt | H | 2.16 | 483 |
| B6 | H | H | n-Pr-O— | H | 2.21 | 497 |
| B7 | H | H | EtHN— | H | 2.23 | 482 |
| B8 | Me$_2$N— | H | H | H | 2.08 | 482 |
| B9 | H | H | Me$_2$N— | H | 2.07 | 482 |
| B10 | EtHN— | H | H | H | 2.12 | 482 |

TABLE C

Compounds of formula (Ih):

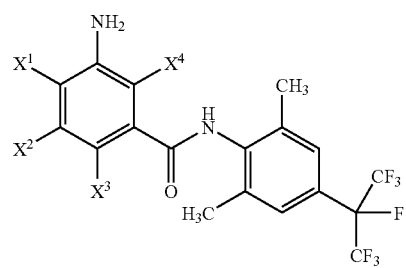

(Ih)

| Compound No. | $X^1$ | $X^2$ | $X^3$ | $X^4$ | RT (min) | $MH^+$ |
|---|---|---|---|---|---|---|
| C1 | H | MeO— | H | MeO— | 2.02 | 469 |
| C2 | MeO— | H | H | H | 1.92 | 439 |
| C3 | H | H | MeO— | MeO— | 1.86 | 469 |
| C4 | H | H | MeO— | H | 1.79 | 439 |
| C5 | H | H | EtO— | H | 1.94 | 453 |
| C6 | H | H | n-Pr—O— | H | 2.05 | 467 |
| C7 | H | H | EtHN— | H | 1.56 | 452 |
| C8 | Me$_2$N— | H | H | H | 1.96 | 452 |
| C9 | H | H | Me$_2$N— | H | 1.75 | 452 |
| C10 | EtHN— | H | H | H | 1.92 | 452 |

TABLE D

Compounds of formula (Ij):

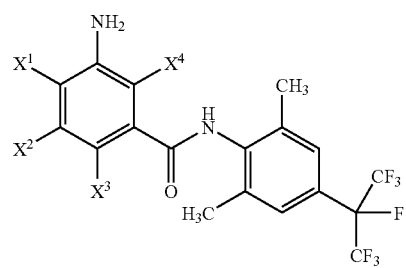

(Ij)

| Compound No. | $Q^1$ | $X^1$ | $X^2$ | $X^3$ | $X^4$ | $R^1$ | $R^2$ | $Y^1$ | $Y^5$ | RT (min) | $MH^+$ |
|---|---|---|---|---|---|---|---|---|---|---|---|
| D1 | 4-fluorophenyl | H | MeO— | H | MeO— | H | H | Et | Et | 2.22 | 619 |
| D2 | 4-fluorophenyl | H | MeO— | H | MeO— | Et | H | Et | Et | 2.30 | 647 |
| D3 | 4-fluorophenyl | H | MeO— | H | MeO— | H | H | —CH$_2$—OCH$_3$ | Me | 2.18 | 621 |

BIOLOGICAL EXAMPLES

This Example illustrates the pesticidal/insecticidal properties of compounds of formula (I). Tests were performed as follows:

*Spodoptera littoralis* (Egyptian cotton leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behaviour, and growth regulation 3 days after treatment (DAT).

The following compounds gave at least 80% control of *Spodoptera littoralis*: A9, A18, A57, A112, D2.

*Heliothis virescens* (Tobacco budworm):

Eggs (0-24 h old) were placed in 24-well microtiter plate on artificial diet and treated with test solutions at an application rate of 200 ppm (concentration in well 18 pm) by pipetting. After an incubation period of 4 days, samples were checked for egg mortality, larval mortality, and growth regulation.

The following compounds gave at least 80% control of *Heliothis virescens*: A2, A7, A8, A9, A16, A23, A61, A103, A112, D1, D2.

*Plutella xylostella* (Diamond back moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality, and growth regulation.

The following compounds gave at least 80% control of *Plutella xylostella*: A9, A16, A18, A57, A90, A101, A106, A112, D1, D2.

*Diabrotica balteata* (Corn root worm):

A24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*: A7, A9, A15, A18, A89, A112, D1, D2.

*Aedes aegypti* (Yellow fever mosquito):

10-15 *Aedes* larvae (L2) together with a nutrition mixture are placed in 96-well microtiter plates. Test solutions at an application rate of 2 ppm were pipetted into the wells. 2 days later, insects were checked for mortality and growth inhibition.

The following compounds gave at least 80% control of *Aedes aegypti*: A7, A8, A9, A16, A18, A112.

The invention claimed is:

1. A compound of formula (I):

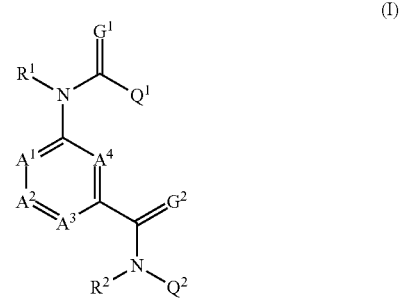

wherein $A^1$, $A^2$, $A^3$ and $A^4$ are independently of one another C—X—$R^3$, C—$R^5$ or nitrogen, provided that at least one of $A^1$, $A^2$, $A^3$ and $A^4$ is C—X—$R^3$ and no more than two of $A^1$, $A^2$, $A^3$ and $A^4$ are nitrogen;

$R^1$ and $R^2$ are independently of one another hydrogen, $C_1$-$C_4$alkyl or $C_1$-$C_4$alkylcarbonyl;

$G^1$ and $G^2$ are independently of one another oxygen or sulfur;

each $R^3$ is independently hydrogen, $C_1$-$C_{12}$alkyl, $C_1$-$C_{12}$haloalkyl, $C_2$-$C_8$alkenyl, $C_2$-$C_8$alkynyl, aryl or aryl substituted by halogen or $C_1$-$C_4$alkyl, or heterocyclyl or heterocyclyl substituted by halogen or $C_1$-$C_4$alkyl;

each X is independently oxygen, sulfur or N—$R^4$; wherein each $R^4$ is independently hydrogen, $C_1$-$C_4$alkyl or $C_1$-$C_4$alkylcarbonyl;

each $R^5$ is independently hydrogen, halogen, $C_1$-$C_4$alkyl or trifluoromethyl;

$Q^1$ is aryl or aryl substituted by one to five substituents $R^6$, which may be the same or different, or $Q^1$ is heterocyclyl or heterocyclyl substituted by one to five substituents $R^6$, which may be the same or different; wherein each $R^6$ is independently cyano, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, $C_1$-$C_4$ alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$ alkylcarbonylamino or phenyl; and $Q^2$ is a moiety of formula (II) or (III)

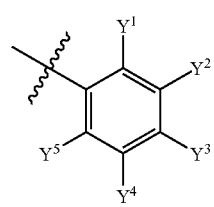

-continued

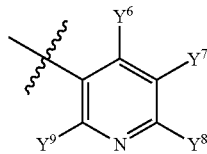
(III)

wherein
$Y^1$ and $Y^5$ are independently of each other cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$ alkylsulfinyl, $C_1$-$C_3$haloalkylsulfinyl, $C_1$-$C_3$alkylsulfonyl or $C_1$-$C_3$haloalkylsulfonyl;
$Y^3$ is $C_2$-$C_6$perfluoroalkyl, $C_1$-$C_6$perfluoroalkylthio, $C_1$-$C_6$perfluoroalkylsulfinyl or $C_1$-$C_6$ perfluoroalkylsulfonyl;
$Y^2$ and $Y^4$ are independently of each other hydrogen, halogen or $C_1$-$C_4$alkyl;
$Y^6$ and $Y^9$ are independently of each other cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$ alkylsulfinyl, $C_1$-$C_3$haloalkylsulfinyl, $C_1$-$C_3$alkylsulfonyl or $C_1$-$C_3$haloalkylsulfonyl;
$Y^8$ is $C_1$-$C_4$haloalkoxy, $C_2$-$C_6$perfluoroalkyl, $C_1$-$C_6$ perfluoroalkylthio, $C_1$-$C_6$perfluoroalkyl-sulfinyl or $C_1$-$C_6$ perfluoroalkylsulfonyl;
$Y^7$ is hydrogen, halogen or $C_1$-$C_4$alkyl;
or salts or N-oxides thereof.

2. A compound according to claim 1 wherein $A^1$ is C—X—$R^3$ or C—$R^5$.
3. A compound according to claim 1 wherein $A^2$ is C—X—$R^3$ or C—$R^5$.
4. A compound according to claim 1 wherein $A^3$ is C—X—$R^3$ or C—$R^5$.
5. A compound according to claim 1 wherein $A^4$ is C—X—$R^3$ or C—$R^5$.
6. A compound according to claim 1 wherein one or two of $A^1$, $A^2$, $A^3$ and $A^4$ are C—X—$R^3$.
7. A compound according to claim 1 wherein $R^1$ is hydrogen, methyl, ethyl or acetyl.
8. A compound according to claim 1 wherein $R^2$ is hydrogen, methyl, ethyl or acetyl.
9. A compound according to claim 1 wherein $G^1$ is oxygen.
10. A compound according to claim 1 wherein $G^2$ is oxygen.
11. A compound according to claim 1 wherein each $R^3$ is independently hydrogen, methyl, ethyl, n-propyl, allyl, phenyl or phenyl mono-substituted by halogen or methyl.
12. A compound according to claim 1 wherein each X is independently oxygen or sulfur.
13. A compound according to claim 1 wherein each $R^4$ is independently hydrogen or methyl.
14. A compound according to claim 1 wherein each $R^5$ is independently hydrogen, fluoro, methyl or trifluoromethyl.
15. A compound according to claim 1 wherein $Q^1$ is 5-bromo-furan-2-yl, 2-bromo-phenyl, 5-bromo-pyrid-3-yl, 2-chloro-5-nitro-phenyl, 2-chloro-phenyl, 3-chloro-phenyl, 2-chloro-pyrid-3-yl, 2-chloro-pyrid-4-yl, 6-chloro-pyrid-3-yl, 5-chloro-thiophen-2-yl, 3-chloro-5-trifluoromethyl-pyrid-2-yl, 4-cyano-phenyl, 2,5-dichloro-phenyl, 2,3-difluoro-phenyl, 1,3-dimethyl-pyrazol-5-yl, 4-fluoro-phenyl, 2-fluoro-pyrid-3-yl, 2-fluoro-3-trifluoromethyl-phenyl, 2-methyl-phenyl, 3-methyl-pyrid-2-yl, 2-methylthio-pyrid-3-yl, 4-nitro-phenyl, phenyl, 1,2,3-thiadiazol-4-yl and thiophen-2-yl.
16. A compound according to claim 1 wherein $Q^2$ is a moiety of formula (II).
17. A compound according to claim 1 wherein $Q^2$ is 2,6-dimethyl-4-perfluoroisopropyl-phenyl.
18. A compound according to claim 1 wherein $Q^2$ is 2,6-diethyl-4-perfluoroisopropyl-phenyl.
19. A compound according to claim 1 wherein $Q^2$ is 4-heptafluoroisopropyl-2-methoxymethyl-6-methyl-phenyl.
20. A method of combating or controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.
21. An insecticidal, acaricidal, nematicidal or molluscicidal composition comprising an insecticidally, acaricidally, nematicidally or molluscicidally effective amount of a compound of formula (I) as defined in claim 1.

* * * * *